US010736544B2

(12) United States Patent
Cramer

(10) Patent No.: US 10,736,544 B2
(45) Date of Patent: Aug. 11, 2020

(54) SYSTEMS AND METHODS FOR FACILITATING REHABILITATION THERAPY

(71) Applicant: The Regents of the University of California, Oakland, CA (US)

(72) Inventor: Steven C. Cramer, Irvine, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 150 days.

(21) Appl. No.: 15/987,846

(22) Filed: May 23, 2018

(65) Prior Publication Data

US 2018/0263535 A1  Sep. 20, 2018

Related U.S. Application Data

(63) Continuation-in-part of application No. 15/254,029, filed on Sep. 1, 2016, now Pat. No. 10,475,352.

(60) Provisional application No. 62/216,177, filed on Sep. 9, 2015.

(51) Int. Cl.
| | |
|---|---|
| *A61B 5/11* | (2006.01) |
| *G16H 20/30* | (2018.01) |
| *G16H 40/67* | (2018.01) |
| *A61B 5/00* | (2006.01) |

(52) U.S. Cl.
CPC .......... *A61B 5/1124* (2013.01); *A61B 5/0022* (2013.01); *A61B 5/1121* (2013.01); *A61B 5/1128* (2013.01); *A61B 5/486* (2013.01); *A61B 5/6887* (2013.01); *A61B 5/7445* (2013.01); *A61B 5/7475* (2013.01); *G16H 20/30* (2018.01); *G16H 40/67* (2018.01); *A61B 5/0077* (2013.01); *A61B 2505/09* (2013.01); *A61B 2562/0219* (2013.01)

(58) Field of Classification Search
CPC ............. G06F 19/3481; G06F 19/3418; A61B 5/1118; A61B 24/0062; A61B 5/1124; A61B 5/0022; A61B 5/1121; A61B 5/1128; A61B 5/486; A61B 5/6887; A61B 5/7445; A61B 5/7475; A61B 5/0077; A61B 2505/09; A61B 2562/0219; G09B 19/0038; G09B 19/003; G16H 20/30; G16H 40/67
USPC ...................................................... 434/247
See application file for complete search history.

(56) References Cited

U.S. PATENT DOCUMENTS

| | | | |
|---|---|---|---|
| 9,311,789 B1 | 4/2016 | Gwin | |
| 9,724,598 B2 | 8/2017 | Burdea | |
| 2005/0065452 A1 | 3/2005 | Thompson | |
| 2006/0287617 A1* | 12/2006 | Taub | A61H 1/02 601/24 |
| 2007/0060445 A1 | 3/2007 | Reinkensmeyer et al. | |

(Continued)

*Primary Examiner* — Jack Yip
(74) *Attorney, Agent, or Firm* — Nguyen Tarbet

(57) ABSTRACT

A rehabilitation system includes a portable patient workstation configured to facilitate in-home rehabilitation therapy. In some embodiments, the workstation includes a computing device and one or more rehabilitation devices. The computing device is configured to generate computer-based tasks associated with one or more in-home exercises. The rehabilitation devices, communicatively coupled to the computing device, includes a sensor that captures movement data for use in evaluating a patient's motor skills when instructed to perform one or more of the tasks.

19 Claims, 12 Drawing Sheets

(56) References Cited

U.S. PATENT DOCUMENTS

| | | | |
|---|---|---|---|
| 2007/0179534 A1* | 8/2007 | Firlik | A61B 5/16 |
| | | | 607/3 |
| 2007/0282228 A1 | 12/2007 | Einav et al. | |
| 2010/0255452 A1* | 10/2010 | Coffey | G09B 5/00 |
| | | | 434/258 |
| 2012/0157263 A1* | 6/2012 | Sivak | G06F 3/014 |
| | | | 482/4 |
| 2013/0143718 A1 | 6/2013 | Pani et al. | |
| 2014/0074180 A1 | 3/2014 | Heldman et al. | |
| 2014/0121018 A1 | 5/2014 | Burdea | |
| 2015/0004581 A1 | 1/2015 | Selman et al. | |
| 2015/0318015 A1* | 11/2015 | Bose | H04N 7/188 |
| | | | 386/248 |
| 2016/0007885 A1* | 1/2016 | Basta | G16H 20/30 |
| | | | 482/5 |
| 2017/0337834 A1 | 11/2017 | Shindi | |
| 2017/0361217 A1 | 12/2017 | Burdea et al. | |

* cited by examiner

SYSTEMS AND METHODS FOR FACILITATING REHABILITATION THERAPY

CROSS-REFERENCE TO RELATED APPLICATION

This application is a continuation-in-part of U.S. patent application Ser. No. 15/254,029 entitled "Systems and Methods for Facilitating Rehabilitation Therapy," which claims priority to U.S. Provisional Application Ser. No. 62/216,177, filed Sep. 9, 2015, the contents of both of which are hereby incorporated by reference herein in their entirety.

NOTICE OF GOVERNMENT-SPONSORED RESEARCH

This invention was made with Government support under Grant No. NS091951, awarded by the National Institutes of Health. The Government has certain rights in the invention.

BACKGROUND

Studies show that patients with a neurological injury, such as due to stroke, multiple sclerosis, trauma, or a degenerative brain condition such as amyotrophic lateral sclerosis, benefit from treatment by a clinician, such as a physical therapist, specializing in rehabilitation therapy combined with home exercising. Unfortunately, most people only receive limited amounts of therapy and similarly perform only limited amounts of home exercise. The reasons for this can include the high cost of and limited access to rehabilitation therapy and low motivation to perform exercises at home. Regardless of the reasons, the limited amounts of rehabilitation therapy provided and home exercising performed often result in the patient not achieving the highest level of recovery.

Traditionally, in-home occupational and physical therapy assignments emphasize repeating exercises with simple devices such as a stretchable band. Unfortunately, no rehabilitation systems currently integrate actual activities of daily living (ADLs) and independent ADLs (iADLs) into a patient's in-home rehabilitation therapy regimen. Some primary reasons for the resistance in adding ADL-based (and/or iADL-based) exercises to the patient's in-home rehabilitation therapy regimen may include (1) the inability of clinicians to receive a sufficient amount of information associated with the performance of in-home exercises directed to ADLs and/or iADLs, and (2) the inability of patients to receive a sufficient amount of feedback on such ADL/iADL-directed exercises. As a result, clinicians are unable to appreciate irregularities in movement unless the patient is performing an ADL or iADL task and the clinician is actually watching the patient during a video conferencing session. However, given that video conferencing provides a single perspective of the patient, subtle movement irregularities may not be appreciated and chances to achieve greater improvements from neurological injury are lost.

BRIEF DESCRIPTION OF THE DRAWINGS

The present disclosure may be better understood with reference to the following figures. Matching reference numerals designate corresponding parts throughout the figures, which are not necessarily drawn to scale.

DETAILED DESCRIPTION

Figure 1:
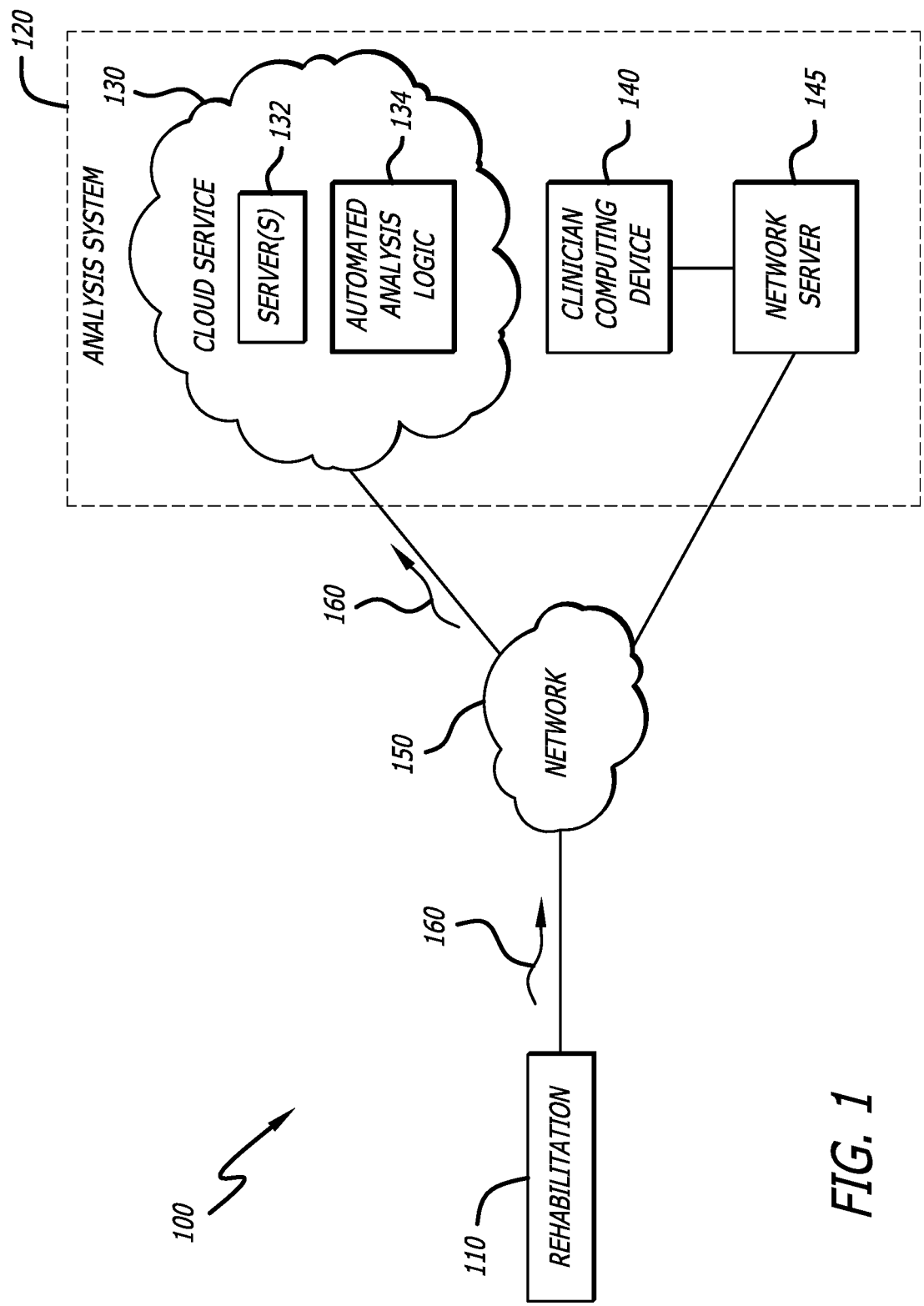
FIG. 1 is a block diagram of an embodiment of a system for facilitating rehabilitation therapy.

Embodiments of the present disclosure generally relate to a rehabilitation system and method that provides holistic rehabilitation therapy to patients, where the rehabilitation therapy features in-home exercises directed to actual activities of daily living (ADLs) and/or independent ADLs (iADLs). ADLs are basic daily activities performed by a person, such as eating, bathing, walking, or dressing for example, while iADLs are more complex activities often performed by a person during the course of a normal day, such as managing money, driving, housekeeping, preparing meals, and proper medication intake. As described herein, the ADL and/or iADL concentrated exercises (hereinafter, "in-home exercises") may be classified as task rehabilitation, arm/leg movement rehabilitation, cognitive rehabilitation, or medicinal compliance.

Herein, the rehabilitation system is configured to monitor, in real-time, the patient's actions during these in-home exercises, notably his or her movements. Additionally, or in the alternative, the rehabilitation system may be configured to collect information associated with the monitored patient's actions during one or more in-home exercises (hereinafter, "performance data"), which is subsequently stored for later evaluation by a clinician. Using the performance data, the clinician may adjust the patient's rehabilitation therapy and confirm medicinal compliance in efforts to improve the patient's recovery level.

According to one embodiment of the disclosure, the rehabilitation system features a plurality of cameras that are positioned at different locations within one or more rooms of a patient's residence (e.g., kitchen, bedroom, bathroom, garage, etc.) or immediately outside that patient's residence (e.g., a portion of the yard, etc.). During in-home exercises, one or more of these cameras are configured to capture video and download video to a computing device (e.g., server). The camera(s) may be continuously gathering video or may be activated during a particular time interval for the in-house exercises. Thereafter, the computing device is configured to transmit, in a secure manner, the captured video to a cloud service.

The cloud service may operate as a private cloud service, which includes machine learning logic or artificial neural network logic that automatically, without human intervention, analyzes the performance data, especially movements by the patient during the in-home exercise. During analysis of the performance data, the cloud service identifies the in-home exercise associated with the performance data by the patient. The cloud service parses the performance data according to one or more activities targeted by the in-home exercises. Thereafter, the cloud service compares a parsed portion(s) of the performance data, which is directed to at least one activity targeted by the in-home exercise, to labeled data associated with the activity. According to one embodiment of the disclosure, the labeled data may include, but is not limited or restricted to movement patterns in performing the specific activity that (i) represents either healthy brain function and/or (ii) is symptomatic of an existing neurological injury or a precursor to a potential neurological injury.

According to another (second) embodiment of the disclosure, the rehabilitation system features a patient workstation including a console and multiple rehabilitation devices. The rehabilitation system further includes a table, a computer, a plurality of cameras, a first display to support video conferencing and video-based therapy games, a second display to support augmented reality, and/or a network connection device, some or all of which may be delivered to the patient's home. As described below, sensors may be integrated into one or more rehabilitation devices to capture movement data associated with the rehabilitation devices or such sensors may be implemented as an adapter attached to or detached from the rehabilitation devices.

Once the workstation is delivered, the patient can use the rehabilitation devices to participate in various computer-based, in-home exercises hosted by the computing device. The in-home exercises are directed, at least in part, to ADL and iADL tasks, which have been specifically selected by a clinician, such as a physical therapist, occupational therapist, physiatrist, nurse, or other medical professional, to exercise parts of the patient's body that are in need of rehabilitation. The in-home exercises may be structured as games that provide motivation to the patient to exercise at home. Moreover, the in-home exercises may involve augmented reality, where virtual images are displayed on the second display to enable the patient to work on leg rehabilitation practice ADL and/or iADL tasks using one or more of the rehabilitation devices.

In some embodiments, the system further includes a clinician control system that comprises software for use by the clinician to tailor a rehabilitation regimen specific to each individual patient. The clinician control system further tracks and analyzes data collected by the cameras positioned within the residence and/or the patient workstation (cameras, sensors, etc.) so that the clinician can evaluate the patient's performance of the in-home exercises. As necessary, the clinician may alter the patient's rehabilitation regimen. In some embodiments, the clinician can further visually and audibly interact with the patient by using the patient workstation as an interface while the patient performs tasks associated within the in-home exercises. This way, the clinician can provide online, synchronous personal assistance to the patient in his or her home even through the clinician is in a different location.

According to another (third) embodiment of the disclosure, the rehabilitation system features one or more data capture devices. One type of data capture device is a wired or wireless sensor, which may be integrated within or attached to a rehabilitation device for use in one or more in-home exercises (e.g., a household item, a portable object represented a household item, etc.). For this embodiment, the sensor may include a communication transceiver, an accelerometer and/or positional logic (e.g., gyroscope and/or compass components). During an in-home exercise using a rehabilitation device including the sensor, performance data is collected and downloaded to the computing device. The performance data may include data associated with the movements of the patient or sensor when the patient is using the rehabilitation device during an in-home exercise (hereinafter, "movement data"). The movement data may include information associated with prescribed metrics (referred to as "metric information" or "parameters"), inclusive of direction, distance, rotation, velocity and/or acceleration of the sensor as well as any incremental changes to such parameters. These parameters may represent the manner in which an ADL (or iADL) task, being part of an in-home exercise, is performed such as a cutting motion, a mixing motion, turning motion, etc. Besides movement data, additional performance data (e.g., grip pressure, hand positioning, foot pressure, weight distribution, etc.) may be captured by other sensors as well.

As described above, according to one embodiment of the disclosure, the computing device is configured to transmit, in a secure manner, the performance data to the cloud service, which includes machine learning logic or artificial neural network logic that analyzes the performance data against known movement patterns associated with healthy brain function (e.g., linear movement, normal, uniform acceleration, etc.) and/or known movement patterns associated with neurological injury (e.g., unsteady movement, acceleration outside normal ranges, etc.). Alternatively, the computing device is configured to transmit, in a secure manner, the movement data to a server accessible by a clinician for analysis against heuristics associated with previously observed movement data representative of healthy brain function and/or neurological injury.

In the following disclosure, various specific embodiments are described. It is to be understood that those embodiments are example implementations of the disclosed inventions and that alternative embodiments are possible. All such embodiments are intended to fall within the scope of this disclosure.

I. Terminology

In the following description, certain terminology is used to describe aspects of the invention. For example, in certain situations, the term "logic" is representative of hardware, firmware and/or software that is configured to perform one or more functions. As hardware, logic may include circuitry having data processing (e.g., processor) or circuitry having data storage functionality (e.g., semiconductor memory). Herein, a "processor" may include, but is not limited or restricted to a central processing unit (CPU), a digital signal processor, an Application Specific Integrated Circuit (ASIC), a field-programmable gate array; an I/O controller (network, disk, memory, keyboard, etc.); receiver, transmitter and/or transceiver circuitry; combinatorial logic, or combinations of one or more of the above components.

Additionally, or in the alternative, "logic" may be in the form of one or more software modules, such as executable code in the form of an operating system component, an executable application, firmware, an application programming interface (API), one or more subroutines, a function, a procedure, an applet, a plug-in, a servlet, a Component Object Model (COM) object, a routine, source code, object code, a shared library/dynamic linked library, a script, a service (e.g., public or private cloud based functionality), or one or more instructions. These software modules may be stored in any type of a suitable non-transitory storage medium, or transitory storage medium (e.g., electrical, optical, acoustical or other form of propagated signals such as carrier waves, infrared signals, or digital signals). Examples of a "non-transitory storage medium" may include, but are not limited or restricted to a programmable circuit; non-persistent storage such as volatile memory (e.g., any type of random access memory "RAM"); persistent storage such as non-volatile memory (e.g., read-only memory ROM," power-backed RAM, flash memory, phase-change memory, etc.), a solid-state drive, hard disk drive, an optical disc drive, or portable memory device; and/or a semiconductor memory. As firmware, the executable code is stored in persistent storage.

The term "computing device" generally refers to an electronic device with data processing and network connectivity functionality. Examples of a computing device may include, but are not limited or restricted to the following: a server; a router or other signal propagation networking equipment (e.g., a wireless or wired access point, cable modem); a set-top box; a video-game console; a computer (e.g., desktop computer or portable computer such as a laptop, tablet, netbook or the like); a smart phone; or wearable technology (e.g., Apple® Iwatch™, Fitbit® fitness wristband, etc.).

The term "interconnect" is a physical or logical communication path to or within a computing device. For instance, the communication path may include a wired and/or wireless connection. Examples of a wired connection include electrical wiring, optical fiber, cable, or bus trace, while a wireless connection may include infrared, radio frequency (RF), or any other wired/wireless signaling mechanism.

The term "segment" may be construed as a portion of video such as an ordered series of frames, a single frame, or a portion of a frame.

Lastly, the terms "or" and "and/or" as used herein are to be interpreted as inclusive or meaning any one or any combination. Therefore, "A, B or C" or "A, B and/or C" may mean any of the following: "A; B; C; A and B; A and C; B and C; A, B and C." An exception to this definition will occur only when a combination of elements, functions, steps or acts are in some way inherently mutually exclusive.

As this invention is susceptible to embodiments of many different forms, it is intended that the present disclosure is to be considered as an example of the principles of the invention and is not intended to limit the invention to the specific embodiments shown and described.

II. General Architecture

Referring to FIG. 1, an exemplary embodiment of a system 100 for facilitating in-home rehabilitation therapy through the performance of ADL and/or iADL activities is shown. Herein, the system 100 generally comprises a rehabilitation system 110 communicatively coupled to an analysis system 120 via a network 150, such as a public wide area network (e.g. internet). The analysis system 120 can comprise substantially any device or combination of devices that can be used to analyze performance data 160 downloaded from the rehabilitation system 110. The performance data 160 may include video or movement data, namely analytic data associated with movements captured by one or more sensors when a patient is performing one or more ADL or iADL tasks during an in-home exercise.

One embodiment of the analysis system 120 may operate as a cloud service 130 (e.g., a private cloud service), which includes one or more servers 132 adapted with automated analysis logic 134 (e.g., machine learning logic, artificial neural network logic, or other artificial intelligence). The automated analysis logic 134 may receive one or more video segments as the performance data 160 from the rehabilitation system 110 and analyze the content of the video segment(s). During such analysis, particular movements of the patient, namely the manner in which activities performed by the patient, are compared against known movement patterns associated with healthy brain function (e.g., heuristics associated with movement in which therapy is no longer necessary) and/or known movement patterns associated with neurological injury (e.g., heuristics associated with movement in which therapy is still necessary).

Another embodiment of the analysis system 120 may include a clinician control system 140 and a network server 145, which is communicatively coupled to the network 150. Herein, the clinician control system 140 may comprise substantially any device that can be used to access and interact with the network server 145. Accordingly, the clinician control system 140 may operate as a computing device (e.g., a desktop computer, a laptop computer, a tablet computer, a smartphone, etc.) coupled to the network server 145. As described in greater detail below, in relation to FIG. 6, the network server 145 (a remote computer) may be configured to store and execute the clinician control system 140, which is deployed as software, for use by one or more clinicians to design rehabilitation therapy regimens as well as monitor and evaluate the progress of patients performing their computer-based activities. Such evaluation may be of downloaded video or analytic data captured during performance of ADL and/or iADL tasks as described below.

Figure 2:
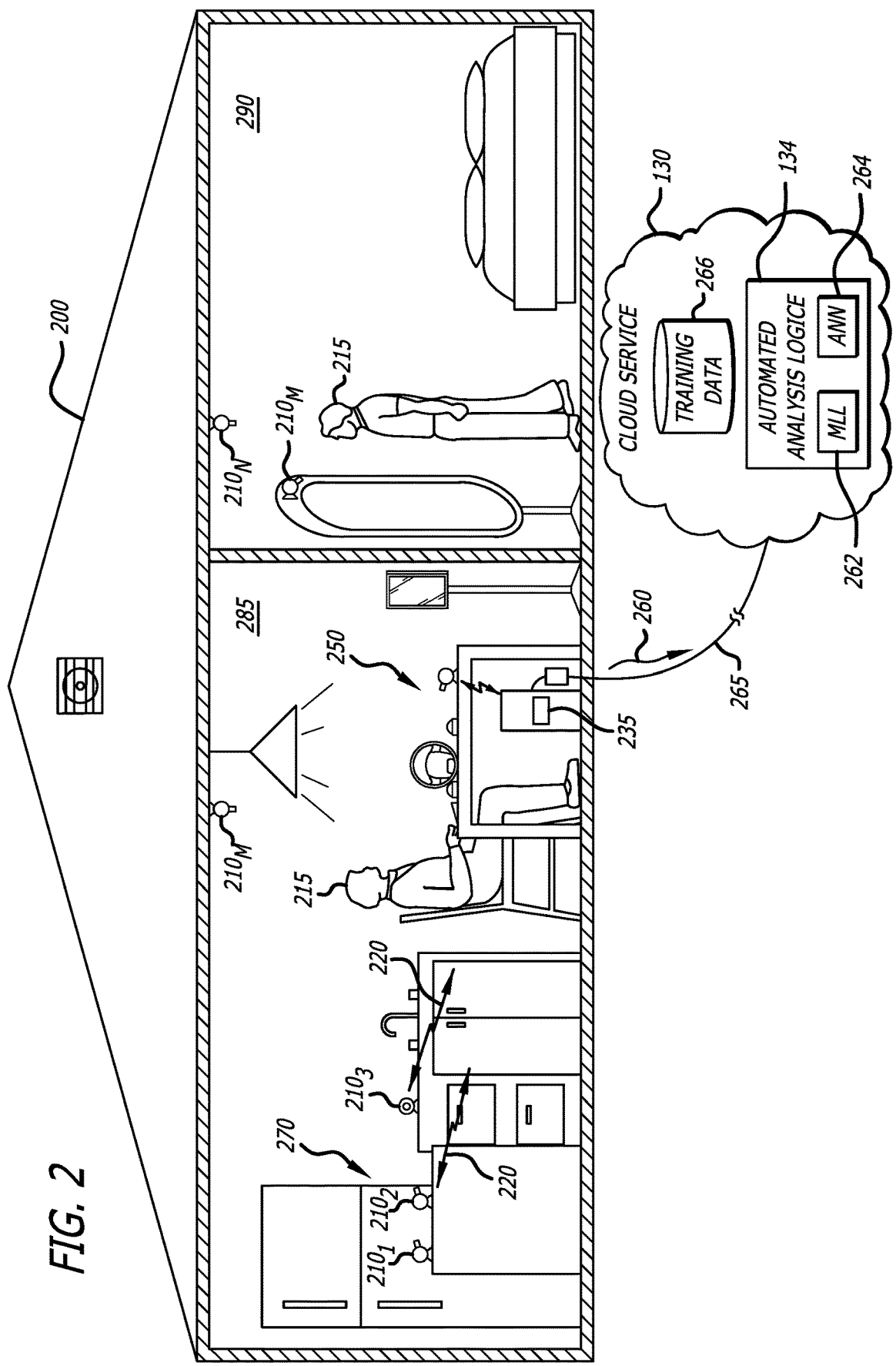
FIG. 2 is an illustrative diagram of a first embodiment of a rehabilitation system of FIG. 1 with one or more cameras to gather images and/or video for cloud based analysis (cloud-based rehabilitation system).

Referring now to FIG. 2, a block diagram of a first embodiment of the rehabilitation system 110 configured to support in-home ADL-based and/or iADL-based tasks is shown. Herein, a residence 200 features multiple rooms with a plurality of cameras $210_1$-$210_N$ (N≥1) deployed within (or proximate to) the residence 200. The cameras $210_1$-$210_N$ are configured to capture video directed to ADL and/or iADL tasks being performed by a patient 215 and the captured video is downloaded over a network 220 to a computing device 230 and/or the cloud service 130. The network 220 may operate as separate peer-to-peer communications between the computing device 230 and each of the cameras $210_1$-$210_N$ (e.g., Bluetooth™ (BT) communications) or may operate as a wired or wireless local area network (LAN) to which the cameras $210_1$-$210_N$ are connected.

The ADL and/or iADL tasks performed by the patient 215 are selected in accordance with a rehabilitation regimen assigned to that patient. According to one embodiment of the disclosure, the patient 215 may receive instructions to perform certain ADL and/or iADL tasks during his or her in-home exercises, where the instructions are generated and provided from therapy software 235 that is hosted by the computing device 230 operating with a patient workstation 250. During execution, the therapy software 235 provides written or auditory instructions to the patient 215 to perform certain ADL and/or iADL tasks for the patient's rehabilitation regimen. Moreover, during performance of the selected ADL and/or iADL tasks, one or more of the cameras $210_1$-$210_N$ may be activated by the computing device 230 to capture video as the patient 215 performs the selected ADL and/or iADL tasks.

According to another embodiment of the disclosure, however, the patient 215 may receive instructions for performing the ADL and/or iADL tasks either from the therapy software 235 being hosted by the analysis system 120 of FIG. 1 (e.g., remote network server 145) or directly from a clinician (e.g., via video conference call using the patient workstation 250, video conferencing or audio communication via a device other than the patient workstation 250 such as a telephone, networked television, or the like). During performance of the selected ADL and/or iADL tasks, one or more of the cameras $210_1$-$210_N$ may be under control of the clinician (via a controlled remote connection to the computing device 230).

Regardless whether instructions to perform ADL (and/or iADL) tasks are conducted locally or remotely, the specific ADL and/or iADL task(s) performed during each instructed in-home exercise is(are) identified. As a result, each video segment captured by a camera $210_1$-$210_N$ activated to monitor movements by the patient is associated with metadata that may be used by the analysis system 120 of FIG. 1 to identify what ADL and/or iADL tasks pertain to each captured video segment. For instance, a task code value may be assigned to each captured video segment to identify the ADL and/or iADL tasks performed during the captured video segment. This task code value may be used by the automated analysis logic 134 (e.g., machine learning logic) or the clinician to focus on particular characteristics that may differ between ADL and iADL tasks.

More specifically, the cameras $210_1$-$210_N$ are configured to monitor the actions and movements of the patient in order to provide video that is downloaded to the computing device 230. In response to receiving one or more video segments, the computing device 230 may be adapted to perform pre-processing operations on the received video segment(s) (e.g., apply a task code value to associate a captured video segment to particular task(s), collect video segments from different cameras and perspectives and identify relationships between these video segments, etc.) to produce captured video content 260. The captured video content 260 may include a series of frames that may be collectively analyzed, individual frames that are analyzed separately from each other, and/or portions of an individual frame that are analyzed separately from each other.

The captured video content 260 is downloaded from the computing device 230 to the cloud service 130 via a network 265. The cloud service 130 may include the automated analysis logic 134; namely, machine learning logic 262, artificial neural network (ANN) logic 264, or other artificial intelligence logic that is adapted to analyze the captured video content against known normal activities and/or movements and/or known abnormal activities and/or movements (generally referred to as "training data"). The known normal activities and/or movements and/or known abnormal activities and/or movements may be stored in a repository 266 available to the automated analysis logic 134.

As an illustrative example, in response to a request by the therapy software 235 operating at the patient workstation 250 or instructions from an out-of-band source (e.g., a telephone call, a Skype™ communication, etc.), the patient 215 may be instructed to perform a particular task at a designated location 270 (e.g., kitchen island). During the patient's travel to the designated location 270, a subset of the plurality of cameras $210_1$-$210_M$ (M<N) are arranged, when activated, to capture video of the patient's gait during his or her walk to the designated location 270. For gait, the captured video content based on video segments collected by one or more of the cameras $210_1$-$210_M$ may feature specific metric information indicative of normal and/or abnormal walking tendencies or fall risks. These metric may include, but are not limited or restricted to walking speed, stride length, stride frequency, smoothness, lateral sway, and/or forward pitch. The metric information may be analyzed by the automated analysis logic 134 within the cloud services 130 to determine the level of risk and ambulatory issues associated with that patient 215.

Such metric information may assist in the pathological analysis of the patient to identify or highlight metrics that require improvement. For instance, during analysis by the cloud service 130, where the patient 215 sways excessively (e.g., greater than a prescribed threshold), this failed metric is identified. After analysis of one or more of the metrics associated with gait, the resultant metric information may be provided to a clinician, in detail or in an actionable summary report that highlights the most salient findings from a fall risk perspective, to help identify more precisely areas in which the patient needs to improve from an ambulatory viewpoint. This information may assist the clinician to adjust ambulatory therapy to assist in correcting issues associated with the patient's gait or may assist in providing information for discussions between the patient and clinician as to rehabilitation progress. As an optional feature, responsive to determining excessive sway, it is contemplated that a computerized voice may be generated from the therapy software 235 and played back on one or more speakers of the patient workstation 250 (described below) that announces walking characteristics that need to be controlled more precisely to remediate problems and monitor whether or not the patient is able to immediately improve on certain metrics.

As further shown in FIG. 2, the patient may be requested to go to any room (e.g., room 285, room 290) in the residence 200 in order to perform ADL or iADL tasks as part of the rehabilitation therapy. The actions and/or movement by the patient may be captured by additional cameras appropriately positioned within a room designated for therapy analysis. This allows for continuous monitoring of movements by the patient 215 as well as actions and/or movements by the patient 215 when performing requested tasks.

Figure 3:
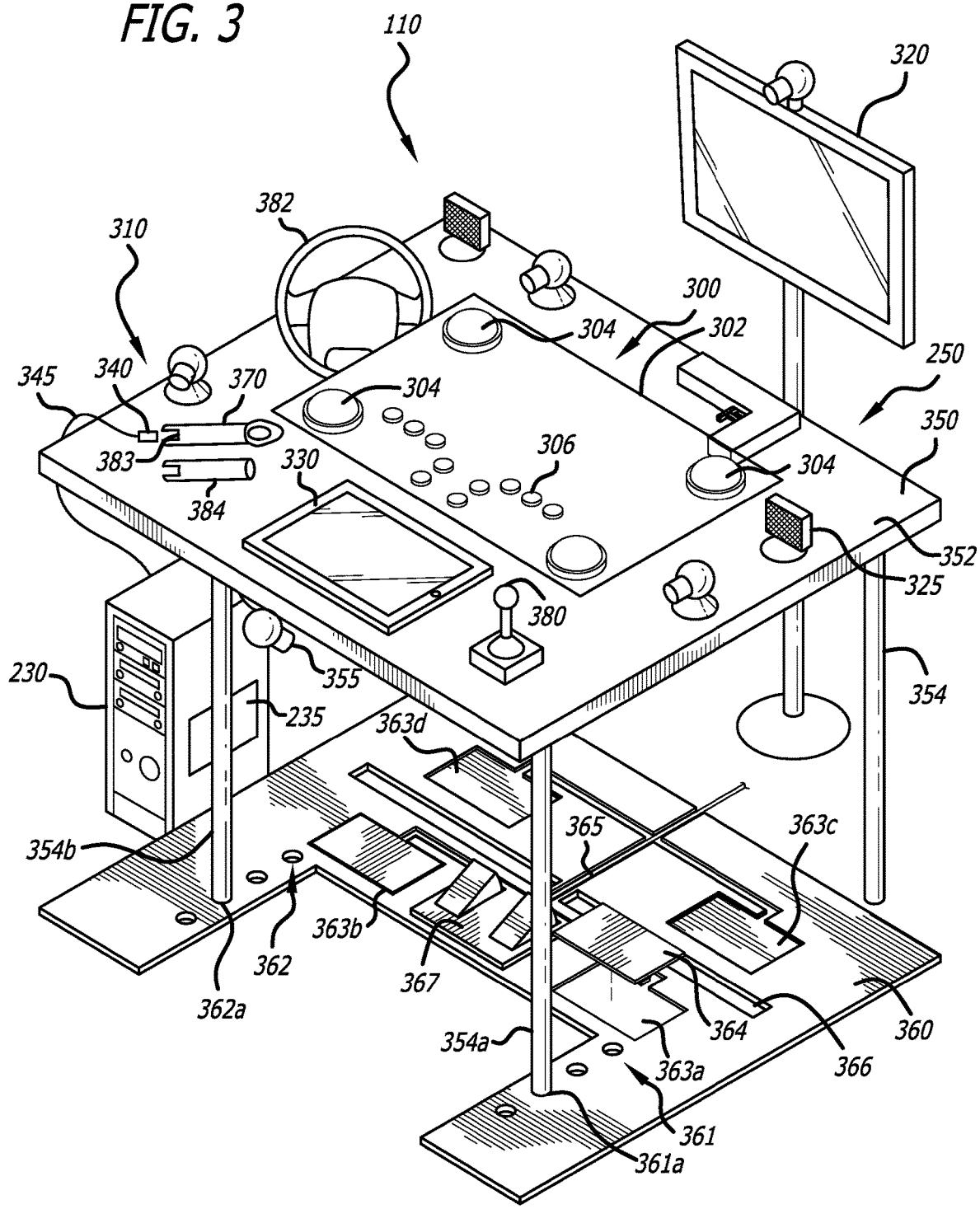
FIG. 3 is an illustrative diagram of a second embodiment of the rehabilitation system of FIG. 1 operating as a patient workstation.

Referring now to FIG. 3, an illustrative diagram of a second embodiment of the rehabilitation system 110 of FIG. 1 operating as the patient workstation 250 is shown. Herein, for this embodiment, the rehabilitation system 110 is a portable, integrated system that comprises components that a patient needs to perform at-home therapy prescribed by the patient's clinician. This is particularly beneficial in cases in which the patient lacks certain facilities, such as a computer and/or internet access, which may be needed to perform activities supported by rehabilitation system 110.

More specifically, the rehabilitation system 110 includes a tabletop console 300, and a plurality of rehabilitation (user interface) devices 310, which are communicatively coupled to the computing device 230. As shown, the coupling may be accomplished with one or more wired interconnects (e.g., cables). Of course, the same functionality can be achieved through wireless interconnects to the computing device 230. Additionally, a first display 320, one or more speakers 325, and a second display 330 are communicatively coupled to the computing device 230. The first display 320 and speakers 325 enable video conferencing between the patient and a clinician. Such video conferencing may be performed while the patient is performing the in-home exercises or at times other than when the in-home exercises are being performed.

As described below, some of the rehabilitation devices 310 may be adapted to receive a sensor 340, which computes metrics associated with the positioning and movement of the rehabilitation device 310 during an in-home exercise controlled by the therapy software 235 executed within the computing device 230 or a remote computer with access to the computing device 230. The sensor 340 is communicatively coupled to the computing device 230 via a wired interconnect 345 or a wireless interconnect (e.g., BT transmitter/receiver pair, BT transmitters, etc.).

With further reference to FIG. 3, the tabletop console 300, in some embodiments, is configured to securely attached to a top surface (tabletop) 352 of a rehabilitation table 350. In some embodiments, the console 300 features a support member 302, which is configured to lie flat on the tabletop 352 and includes multiple integrated rehabilitation devices that, when used, provide measured inputs into the computing device 230. In the embodiment of FIG. 3, the integrated rehabilitation devices include multiple (e.g., 4) distantly spaced large buttons 304 and multiple (e.g., 10) closely spaced small buttons 306. Each of these integrated rehabilitation devices is physically mounted to the support member 302 and cannot be removed from the support member 302 without console disassembly. In addition, each of these devices is connected to the computing device 230 with one or more cables (not visible in FIG. 3).

In some embodiments, the large buttons 304 are positioned on the tabletop console 300 so as to define four corners of a rectangular space on the surface of the support member 302. This space can, for example, be approximately 1 to 3 feet wide and approximately 1 to 2 foot deep from the perspective of a patient seated at the table 350. In some embodiments, the large buttons 304 can be illuminated (e.g., with different colors), either when commanded to do so by the computing device 230 or when pressed or hit by the patient, depending upon the activity in which the patient is participating.

The small buttons 306 can be arranged in two generally lateral rows that are generally contained within the rectangular space defined by the large buttons 304. As shown in FIG. 3, the rows can be curved so as to be ergonomically adapted to receive the patient's fingertips. In such a case, the small buttons 306 can be pressed by individual fingers in similar manner to keyboard keys. Although not shown, the second display 330 may be integrated as part of the support member 302 to allow for auxiliary reality (AR) in-home exercises as described below.

More specifically, as shown in FIG. 3, the rehabilitation table 350 includes the generally horizontal tabletop 352 supported by a plurality of legs 354 extending from the tabletop 352 and stabilized through a rehabilitation mat 360. In some embodiments, the rehabilitation table 350 may be a foldable table that can be easily transported and set up in the patient's home. The table 350 may be configured to support the tabletop console 300 and/or computing device 230, which is configured to store software that can be executed to enable the patient to participate in computer-based activities, including computer games.

A distal end for a first leg 354a of the plurality of legs 354 is sized for placement into a corresponding precut aperture 361a of a first set of linear apertures 361 precut within the rehabilitation mat 360. A distal end for a second leg 354b of the plurality of legs 354 is sized for placement into a precut aperture 362a of a second set of linear apertures 362, which corresponds to and is aligned with the first set of linear precut apertures 361. Collectively, the sets of precut apertures 361 and 362 are provided with a depth that limits lateral movement of the table 350 despite the patient applying a force against the tabletop 352 of the table 350 when the distal ends of the leg pairs 354a-354b are inserted into corresponding precut apertures (e.g., apertures 361a and 362a).

As shown, an embodiment of the rehabilitation mat 360 includes at least the first and second sets of aligned precut apertures (e.g. apertures 361a and 362a) and a third set of precut aperture 363. Each of the precut apertures 363 is positioned and sized to receive a touchpad 364. Also, a channel 365 feeds into each of the precut apertures 363 to allow for insertion of one or more wired interconnects (e.g., cables, power cords, etc.) which connect the touchpad 364 to the computing device 230 and/or a power outlet (not shown). Herein, the third set of precut apertures 363 is illustrated as four precut apertures 363a-363d although it is contemplated that the third set of precut apertures 363 may be a single precut aperture.

A fourth set of precut apertures 366 is formed in the rehabilitation mat 360, which may operate as a groove for connecting rehabilitation devices for use with in-home exercises to improve leg function. A pair of foot pedals 367 may be placed on the rehabilitation mat 360, which are used as automobile pedals for practicing driving as an iADL task.

While the first display 320 is provided to allow for communications between the clinician and the patient through video conferencing, it is contemplated that the first display 320 may also be utilized in order to provide written (visible) instructions to the patient. The second display 330 is provided to allow for augmented reality (AR) in which one or more computer generated images are rendered and combined with an image captured by a camera 355. Hence, where the second display 330 is a touch-activated display, one or more virtual images are rendered and inserted as an overlay (or applied as part of a background) of the image captured by the camera 355 and operations performed on a surface of the second display 330 that are directed to virtual items illustrated on the second display 330 may be measured.

As can be appreciated from FIG. 3, the rehabilitation system 110 includes one or more rehabilitation (user interface) devices 310 that are not mounted to the support member 302 and, therefore, is not part of the console 300. These rehabilitation devices 310 may include a portable object 370 represented a household item (e.g., plastic spatula, plastic cooking spoon, plastic carving knife, etc.) to which a sensor 340 may be removably coupled in order to receive movement data associated with the sensor 340 for use in evaluating the patient's motor skills when instructed to perform in-house exercises, such as AR tasks provided by the second display 330. Each sensor 340 is configured to capture movement data associated with a corresponding rehabilitation device (e.g., portable object 370). Herein, each of the portable objects 370 may include a preformed cavity 382 sized to receive and retain the sensor 340 or the sensor 340 may be attached to the portable object 370 by any type of fastener (e.g., magnetic, clip, Velcro® strap, adhesive, etc.).

Other rehabilitation devices 310 may operate as user interfaces such as a joystick device 380, a steering wheel 382, or a grip tester 384 (e.g., a member including one or more force sensors, such as force transducers, that can measure the force with which the patient squeezes the member with his or her hand or fingers). The steering wheel 382 and corresponding foot pedals 367 are available in order to provide the patient with equipment to perform exercises directed to a specific iADL task (e.g., driving), which is a combination of arm/leg movements as well as cognitive reasoning in which multiple actions are performed simultaneously.

Figure 4:
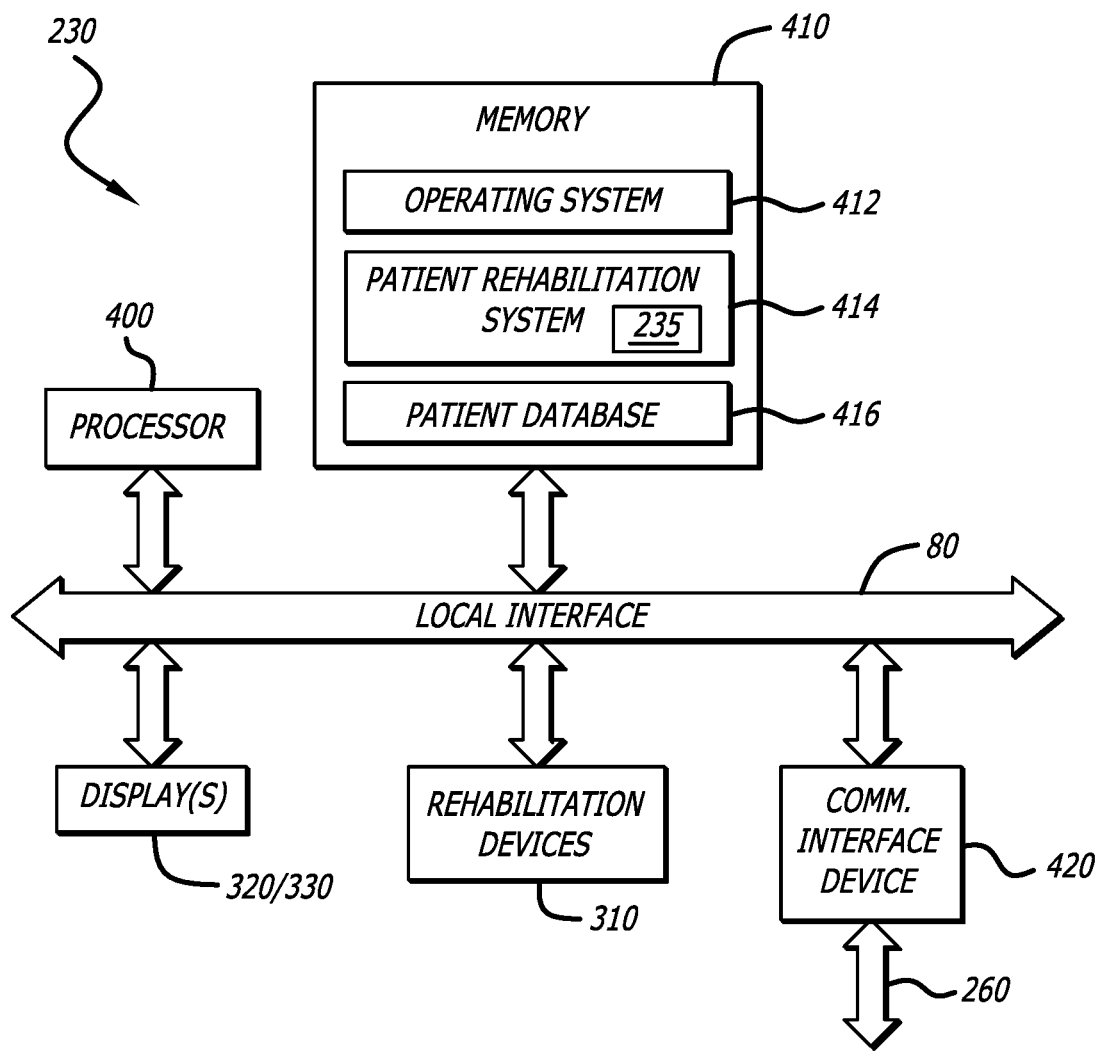
FIG. 4 is an illustrative block diagram of an embodiment of the architecture of the computing device operating with the rehabilitation system of FIG. 3.

Referring now to FIG. 4, an illustrative block diagram of an embodiment of an architecture of the computing device 230 associated with the patient workstation 250 of FIG. 3 is shown. Herein, the computing device 230 includes a processor 400, a memory 410, and a communication interface device 420 (e.g., a network card) interconnected by a local interface (e.g., wired interconnect such as a bus). The memory 410 (a non-transitory computer-readable medium) stores an operating system 412 and a patient rehabilitation system 414. The patient rehabilitation system 414 comprises one or more software programs (logic and/or executable instructions) that facilitate the aforementioned computer-based activities. In some embodiments, the patient rehabilitation system 414 comprises therapy software 235 that may be adapted to control one or more wireless cameras 210$_1$-210$_N$ to capture video segments or establish communications with one or more rehabilitation devices 310.

Additionally, the patient rehabilitation system 414 comprises one or more software programs that collect and store (e.g., in a local patient database 416) usage data for the patient workstation 250. This usage data can comprise any information that may be useful to the patient or the physical therapist in evaluating the patient's progress. Examples of such usage data may include, but is not limited or restricted to (i) times at which the patient uses the workstation 250, (ii) durations of time the patient uses the workstation 250, (iii) the manner in which the patient uses the workstation 250, (iv) the ADL and/or iADL tasks targeted by the in-home exercises conducted by the patient using the workstation 250, (v) rehabilitation devices 310 (portable objects 360) used by the patient while performing the ADL and/or iADL tasks, and/or (vi) analytic data that gauges the patient's skill in performing the ADL and/or iADL tasks. Of course, other information can be collected and stored, if desired.

The patient rehabilitation system 414 further comprises one or more software programs that transmit the collected data to the analysis system 120 of FIGS. 1-2 via network 260 from which the patient's clinician can access. In some embodiments, the analysis system 120 may include the cloud service 130 or the network server 145 of FIG. 1. In such a case, the data can be transmitted with the communication interface device 420 over the network 260. The data can be transmitted in a variety of ways. In some embodiments, the data can be transferred in real time as it is collected. In other embodiments, the data can be collected and stored locally in the local patient database 416 and intermittently transferred, for example, at one or more particular times of day.

Figure 5A:
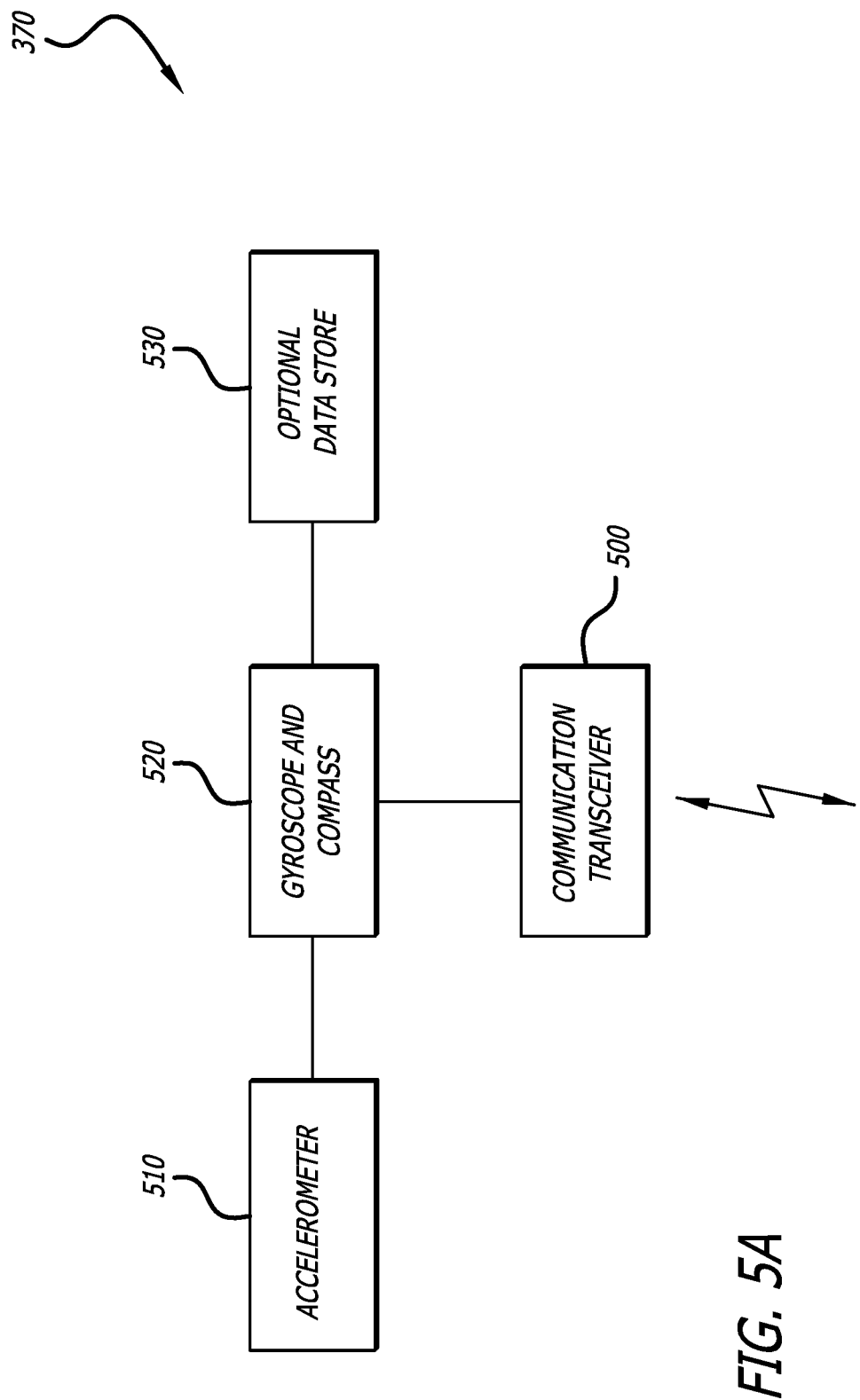
FIG. 5A is an illustrative block diagram of a third embodiment of the rehabilitation system of FIG. 1 operating as a sensor that is gathering and providing movement data to a rehabilitation device (sensor rehabilitation system).

Referring to FIG. 5A, an illustrative block diagram of an embodiment of the sensor 340 is shown. The sensor 340 may include a communication transceiver 500, an accelerometer 510, a gyroscope and compass component set 520, and optional data store (storage) 530. As shown, the communication transceiver 500 may be implemented as a physical device that enables a physical connection between the sensor 340 and a targeted computer (e.g., computing device 230 of FIG. 2) via a wired or wireless interconnect. For this embodiment, the communication transceiver 500 may be configured as a connector adapted to receive a corresponding mating connector attached to an end of the wired interconnect. Alternatively, for another embodiment, the communication transceiver 500 may be adapted as a wireless transceiver that allows for receipt and transmission of wireless signals with the computing device 230.

As further shown in FIG. 5A, the accelerometer 510 is implemented to measure proper acceleration of the portable object 370 including the sensor 340; namely a rate of change of the velocity (movement) of the portable object 370 (rehabilitation device) and changes in position. As a result, the accelerator 510 is adapted to measure changes in linear movement. Operating in combination with the accelerometer 510, the gyroscope and compass combination 520 is configured to measure either changes in orientation or changes in rotational velocity. As an illustrative example, the accelerometer 510 may obtain metric information (parameters) associated with changes caused by discrete linear movement of the portable object 370 being one of the rehabilitation devices 310 (e.g., forward, backward, lateral, tilting, etc.) while the gyroscope and compass combination 520 may obtain metric information associated with changes in angular rotation of the rehabilitation device (e.g., annular rotation such as simulating mixing food items. As a result, collectively, the accelerometer 510 and gyroscope and compass combination 520 enable movement data to be captured and routed via the communication transceiver 500 to the computing device 230 and rerouted to the private cloud or directly to a server that is controlled by the clinician. Optionally, the data store 530 may be positioned in the sensor 500 to enable buffering of the data and downloading of the data after a prescribed task has been completed or after a predetermined amount of time has elapsed.

Figure 5B:
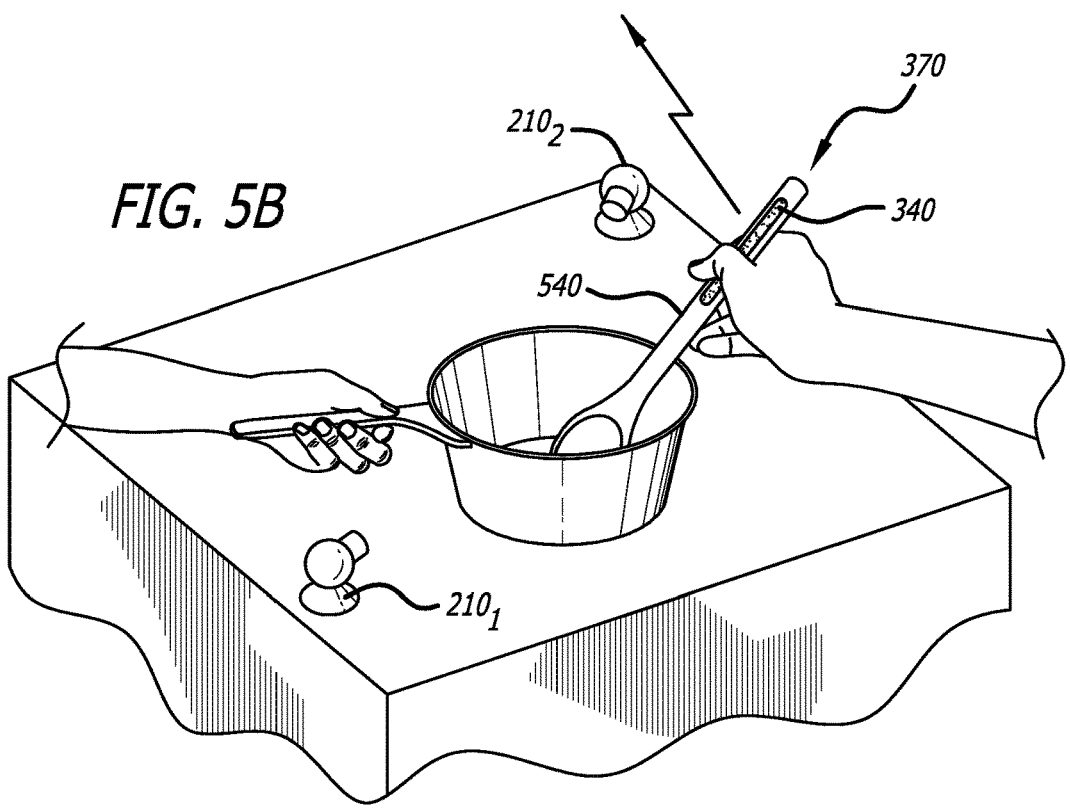
FIG. 5B is a block diagram of a first exemplary sensor integrated as part of the rehabilitation device being a household item.

Referring now to FIG. 5B, a first illustrative embodiment of the sensor 340 positioned within the portable object (rehabilitation device) 370 represented as a plastic stirring spoon is shown. Herein, the sensor 340 is integrated into a handle 540 of the portable plastic spoon 370 to monitor its movement during use in one or more in-home iADL tasks. For instance, the sensor 340 may determine metric information directed to the angular orientation of the portable plastic spoon 370 from vertical during use in an iADL task, the angular movement of the portable plastic spoon 370, the frequency or rotational speed of the portable plastic spoon 370 during use in an iADL task, or the like. Additionally, one or more cameras 210₁-210₂ may be positioned to capture video associated with the performance of the iADL task by a patient and download the video to the computing device (not shown) for local analysis or remote analysis by machine learning or artificial neural network logic deployed in the cloud services 130 of FIG. 1 in order to ascertain what activities being performed by the patient during the iADL task require less or more therapy.

Figure 5C:
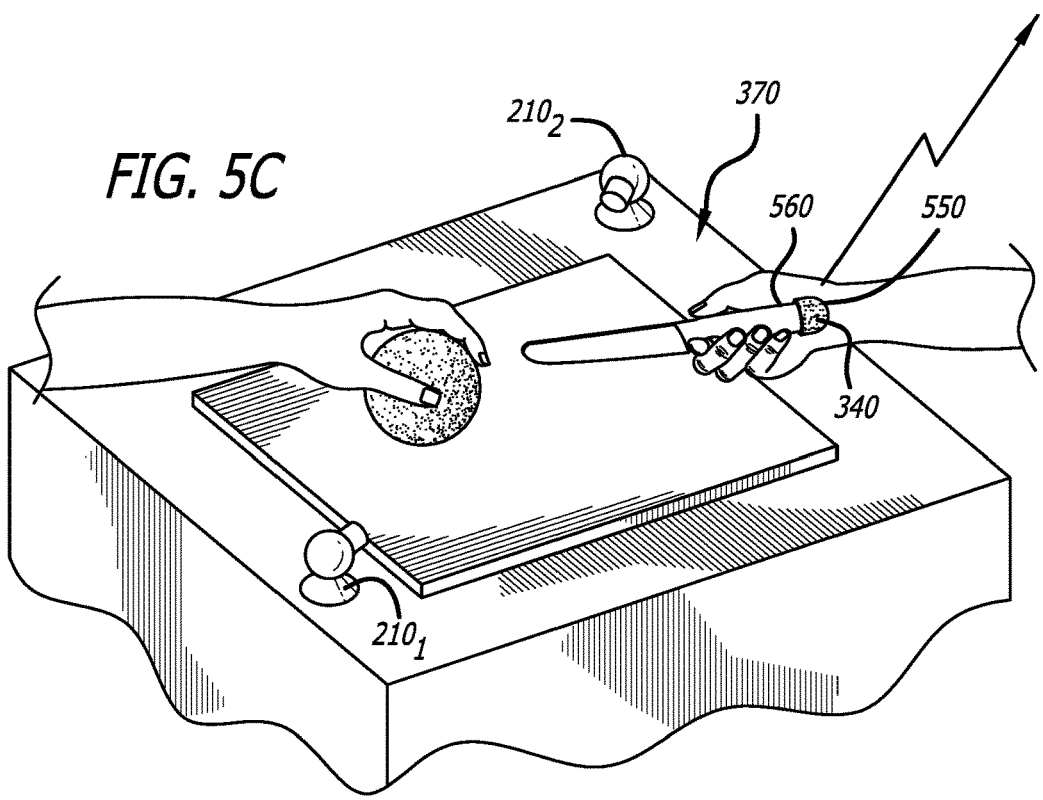
FIG. 5C is a block diagram of a second exemplary sensor deployed on the rehabilitation device being a household item.

Referring to FIG. 5C, a second illustrative embodiment of the sensor 340 positioned on a portable object (rehabilitation device) 370 represented as a portable plastic knife for use during one or more in-home iADL tasks is shown. Herein, the sensor 340 is inserted as part of a flexible sleeve 550 that is positioned over a portion of the portable plastic knife 370. For this embodiment, the sleeve 550 may be formed from any flexible material (e.g., silicone, cloth, etc.) or a rigid material (e.g., hardened plastic sleeve), which is sized for placement over an elongated handle 560 of the portable plastic knife 370. For use of use, the communication transceiver 500 of the sensor 340, as shown in FIG. 5A, includes a Bluetooth™ transceiver to allow for wireless transmission of metrics captured during use of the portable plastic knife 370 during the iADL task(s).

For example, with a cutting iADL task as shown in FIG. 5C, the parameters associated with specific metrics (metric information) may be collected from camera(s) 210₁-210₂ and/or one or more sensors (not shown) embedded within the sleeve 550 surrounding the portable plastic knife 370. In lieu or in addition to the parameters collected by the camera(s) 210₁-210₂ and/or sensor(s) 340 within the sleeve 550, it is contemplated that the additional metric information may be collected from one or more sensors (not shown) embedded in the portable plastic knife 370, one or more body worn sensors that capture specific limb movements and joint angles, or any combination thereof. This metric information can be used to improve patient outcomes in several ways, e.g., by giving tactile, auditory, visual, or combined feedback as the patient deviates from normal usage (where "normal usage" may be adjusted by the clinician prior to performance of the iADL task). For example, a patient capable of performing at an upper end of the functional spectrum may be asked to make rapid cuts, spaced three centimeters apart, to a food item (real or virtual being projected onto the table). The depth of cuts, the stability of the hand holding the food item down, whether the knife rotates towards the subject's midline or away from the body during cutting, and the force of the grip upon the knife (both average grip strength and consistency of grip strength across the various phases of cutting) may be metrics determined by one or more sensors associated with the portable plastic knife 370.

Besides capturing the metric information as described above, the rehabilitation device 370 may be configured to receive feedback during performance of the ADL and/or iADL task. The feedback may be auditory, visual, or tactile in nature (or any combination of these). For example, the portable object (rehabilitation device) 370 may be implemented with vibration logic, which is adapted to receive signaling to vibrate the portable object 370 in response to improper hand placement (e.g., improper location, excess squeeze force, etc.). Additionally, or in the alternative, the portable object 370 may be implemented with one or more speakers that generate an audible sound in response to rotation of a blade of the portable plastic knife 370 exceeding clinician-selected threshold, or generate a vibration upon failing to move correctly per task instructions. Such feedback might also occur when the patient talks to the clinician live/phone/videoconference.

Figure 6:
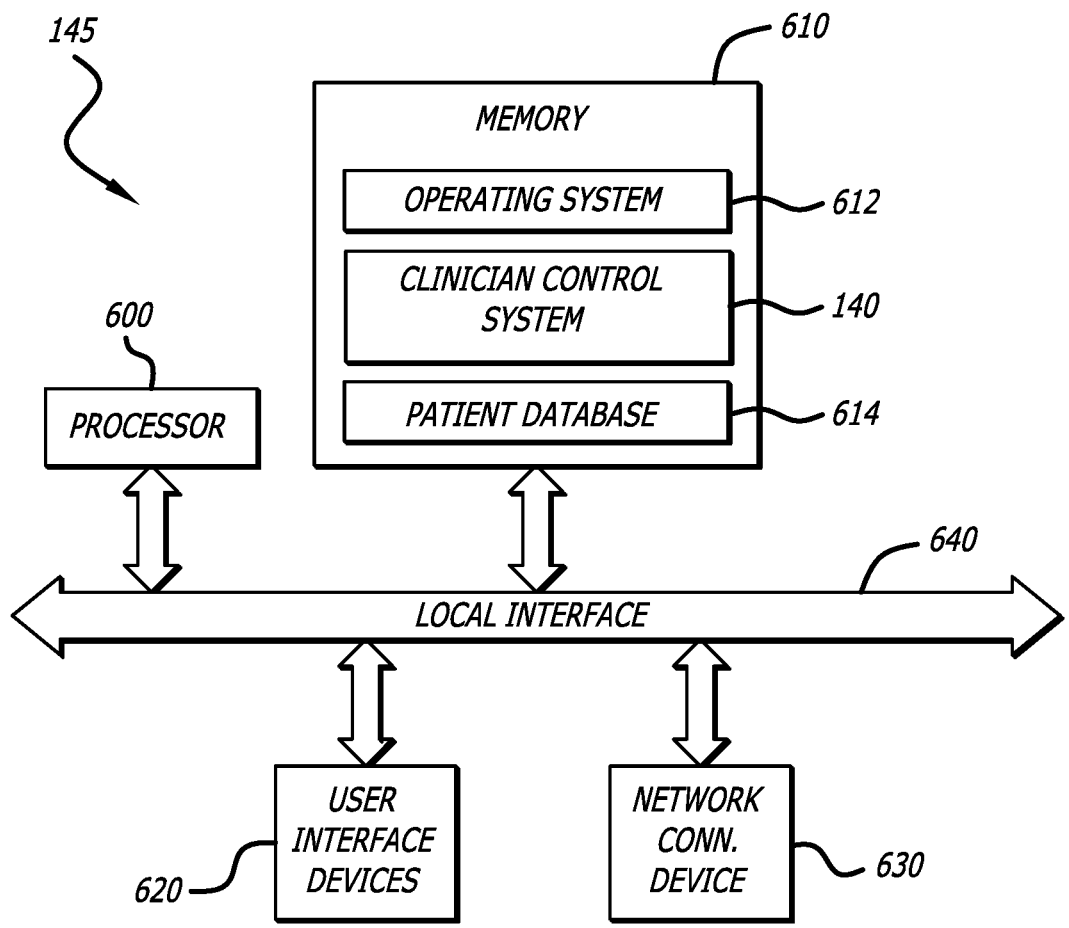
FIG. 6 is a block diagram of an embodiment of an architecture of the network server of the system of FIG. 1.

As shown in FIG. 6, an illustrative embodiment of the architecture for the network server 145 is shown. Herein, this architecture is similar to the architecture of the computing device 230 shown in FIG. 4. Accordingly, the network server 145 includes a processor 600, memory 610, user interface devices 620, and a network connection device 630, each of which is connected to a local interface 640.

The memory 610 (a non-transitory computer-readable medium) stores an operating system 612 and the clinician control system 140. The clinician control system 140 comprises one or more software programs (logic and/or executable instructions) that enable clinicians who access the network server 145 to custom tailor rehabilitation regimens for patients. As described in greater detail below, the clinicians can design the rehabilitation regimens to include particular exercises, games, and rehabilitation devices so that the patient can, according to the regimen, perform specific actions that are explicitly selected to rehabilitate one or more parts of the body. In some embodiments, the clinician control system 140 includes one or more algorithms that assist the clinician in selecting the exercises, games, and rehabilitation devices for the patient based upon the results of a physical examination of the patient.

The clinician control system 140 further comprises one or more software programs that are configured to analyze the parameters (metric information) collected by one or more patient workstations and provide qualitative and/or quantitative information that can be used to assess the patient's condition and progress with his or her rehabilitation therapy.

The memory 610 further includes a patient database 614 in which the data and analysis for multiple patients can be stored on a patient-by-patient basis. In some embodiments, this data and analysis can be shared with patient management software so that the data and analysis can be added to each individual patient's electronic medical file.

Having described example embodiments of a system above, examples of operation of the system will now be discussed. As mentioned above, a clinician can access the software of the clinician control system 140 to design a rehabilitation regimen for a patient and track the patient's progress. Regarding treatment planning, the clinician can plan the patient's treatment based upon the patient's condition. To assess this condition, the clinician can conduct an in-person physical examination of the patient, which may be conducted in the clinician's office, the patient's home, or another location. In cases in which the patient is an individual with stroke, the clinician can perform a Fugl-Meyer assessment with which various patient movements are rated from "0" to "2," where "0" indicates that the patient cannot perform the movement, "1" indicates that the patient can partially perform the movement, and "2" indicates that the patient can fully perform the movement. If the patient has a different neurological injury as the basis for rehabilitation therapy, then an appropriate corresponding assessment can be scored in this manner. In some embodiments, the clinician control system 140 comprises one or more algorithms that are designed to receive these scores as inputs and automatically provide therapy recommendations, which are directed to in-home rehabilitation exercises and/or (i)ADL tasks thereof, to the clinician based upon the scores. In such a case, the clinician can enter the various scores into a suitable screen of the clinician control system 140 for subsequent storage in the patient database 614.

III. In-Home Rehabilitation Exercises

Figure 7A:
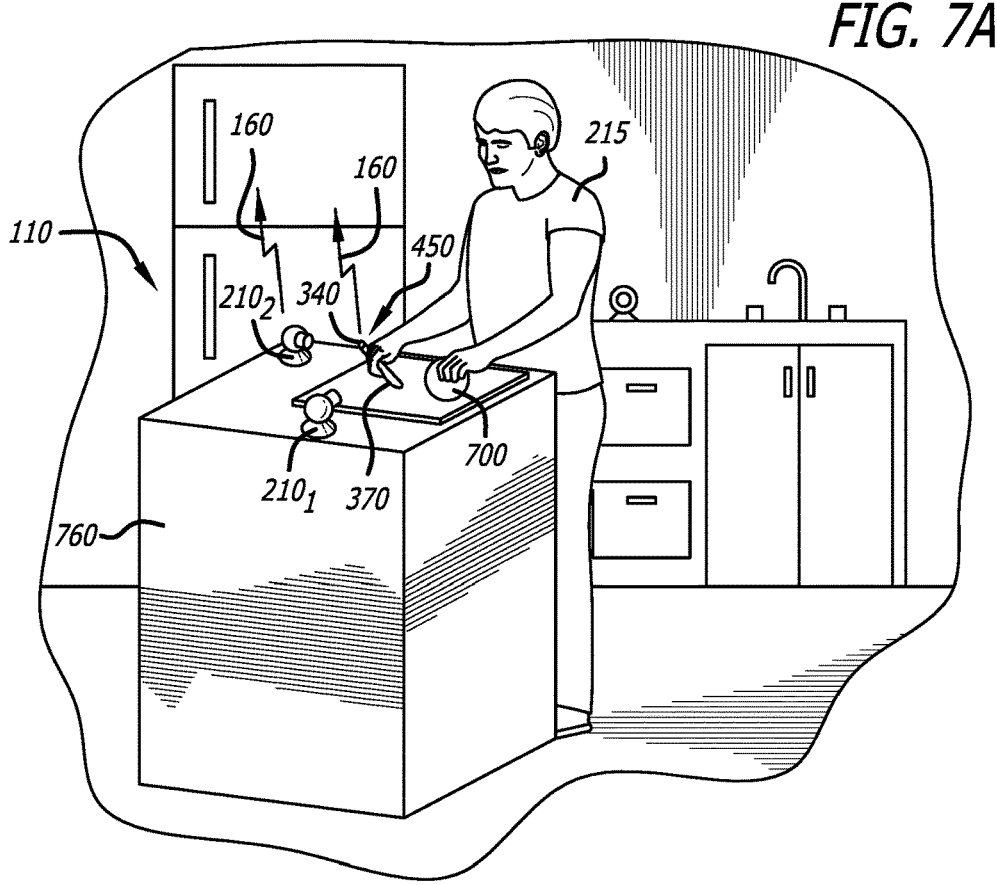
FIG. 7A is an illustrative diagram of a rehabilitation system conducting an in-home exercise directed to task rehabilitation and results of the in-home exercise being collected for analysis.

Referring now to FIG. 7A, an illustrative diagram of the rehabilitation system 110 for use in task rehabilitation is shown. Herein, where the patient is capable of performing at an upper end of a functional spectrum, the in-home exercises may be directed to an iADL task being performed using the physical object. As shown, the iADL task may be directed to the handling of the portable plastic knife 370 for cutting of a food item 700 with a consistency that is easy to penetrate, such as a pear for example. Herein, during the iADL task, performance data 160 may be collected by the cameras $210_1$-$210_2$ positioned on a counter (e.g., kitchen island 310) and/or one or more wireless sensors 340 placed with the sleeve 450 installed on a handle of the plastic kitchen knife 370.

According to this rehabilitation system 110, during the in-home exercise, the cameras $210_1$-$210_2$ are configured to capture video of the patient 215 performing specific cutting instructions in which the tilt of the knife as well as frequency, acceleration, stability of the portable plastic knife 370 during cutting movement is captured for analysis by the (private) cloud service. Furthermore, the wireless sensors 340 collect parameters associated with the metrics selected for the iADL task.

As described herein, the collected metric information involves characteristics related to safe cutting practices, including (i) precision in placement of the knife 370 relative to target (e.g., a pear) in a three-dimensional space, (ii) the force of the hand's grip upon the handle 450 of the knife 370, (iii) the distance/velocity/acceleration of knife movements, (iv) consistency of the knife movements (e.g., steadiness of the hand), (v) positioning of the second hand, (vi) angular adjustment of the knife during cutting, or the like. The collected parameters may be used to improve patient outcomes by giving tactile, auditory, visual, or combined feedback as the patient deviates from an expected performance level. The performance data 160 from both sources (e.g., cameras, sensors, etc.) may be correlated to provide information to the clinician to determine an ability level of the patient and adjust his or her rehabilitation regimen to improve on certain skill sets.

Figure 7B:
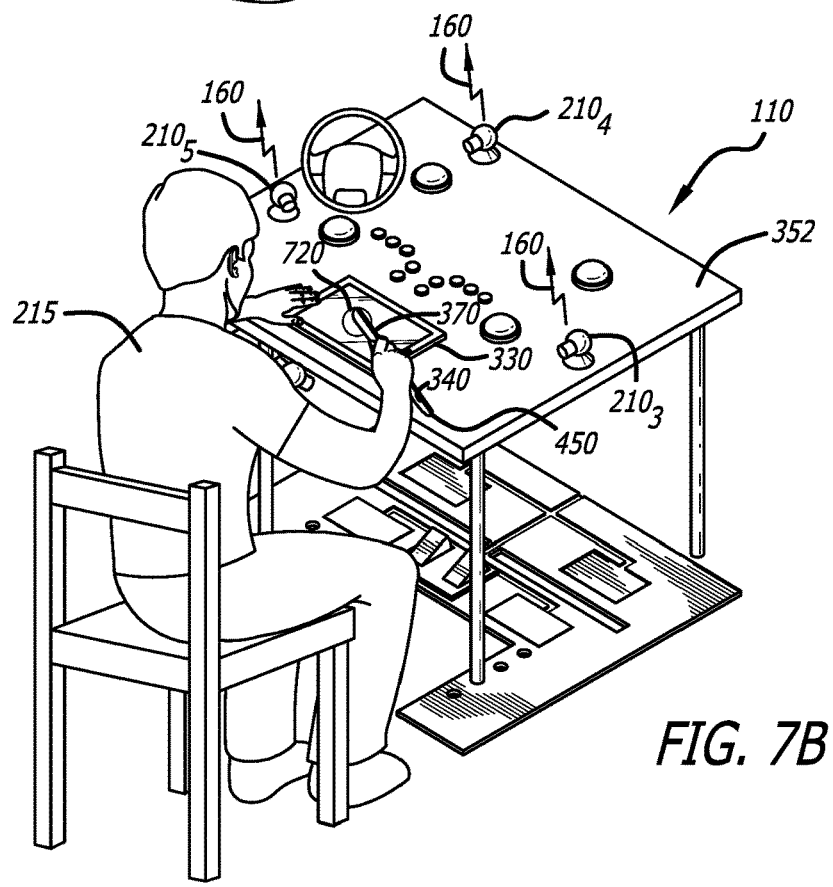
FIG. 7B is an illustrative diagram of a rehabilitation system including a patient workstation conducting an in-home exercise directed to task rehabilitation and results of the in-home exercise being collected for analysis.

As shown in FIG. 7B, an illustrative diagram of another rehabilitation system for use in task rehabilitation is shown. Herein, the in-home exercises may be directed to an iADL task being performed on a virtual object (e.g., virtual representation of a food item) as an AR task using the second display 330. Hence, the iADL task may be directed to the handling of the portable plastic knife 370 for cutting of a virtual food item 720. Herein, during the iADL task, performance data 160 may be collected by the cameras $210_3$-$210_5$ positioned on the tabletop 352 and/or one or more wireless sensors 340 placed with the sleeve 450 installed on a handle of the portable plastic knife 370.

According to this rehabilitation system 110, during the in-home exercise, the cameras $210_3$-$210_5$ are configured to capture video of the patient 215 performing specific cutting movements as described above. Where the second display 330 is a touch screen, the positioning of the knife blade (tilt, alignment, etc.) with respect to displayed cutting patterns to be performed on the virtual food item 720 may be determined by the second display 330 (e.g., based on captured image information, captured data from contact with a touch-sensitive second display 330, etc.) as well as by the wireless sensors 340 as described above.

Figure 8A:
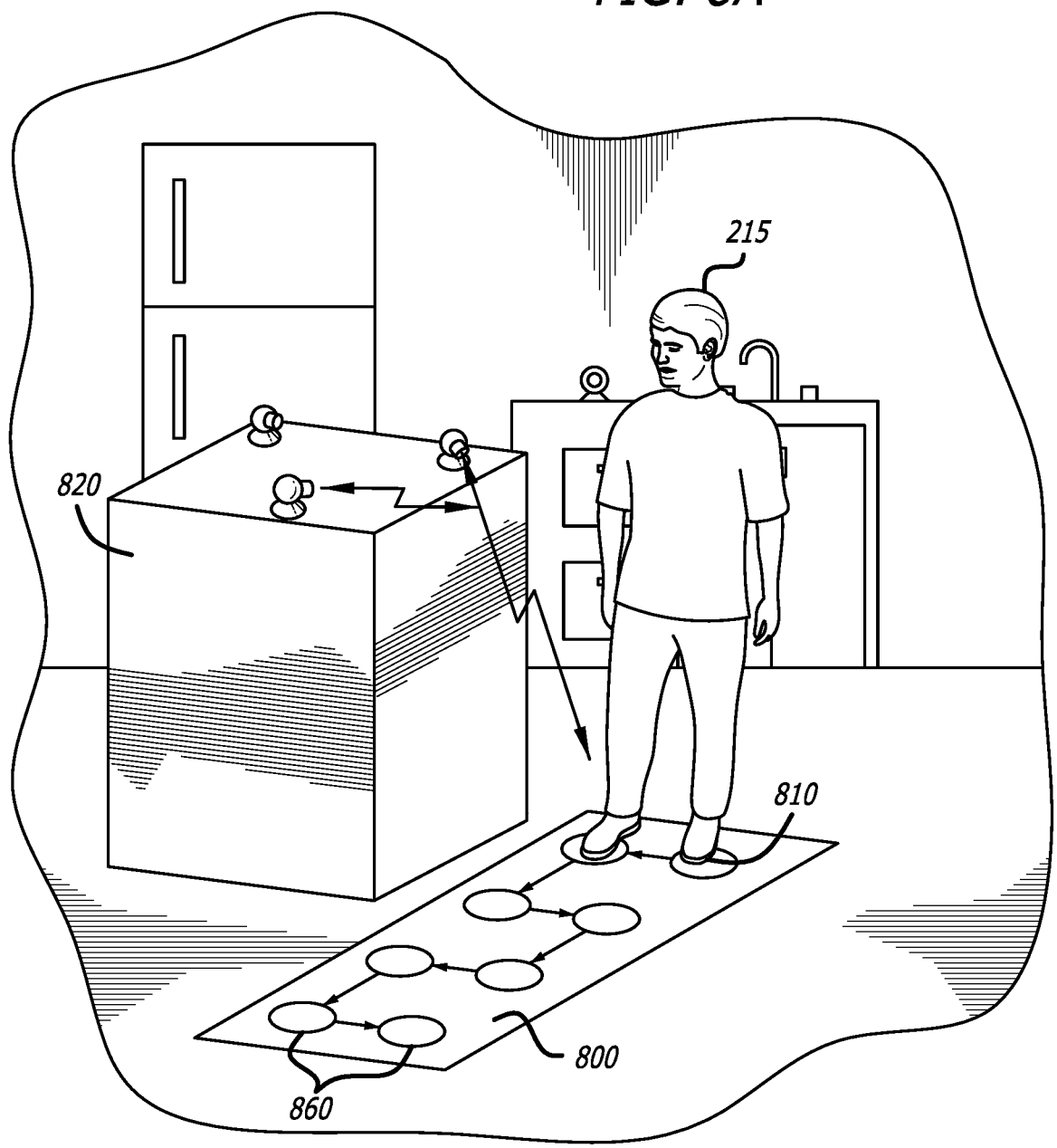
FIG. 8A is an illustrative diagram of a rehabilitation system conducting an in-home exercise directed to leg rehabilitation and results of the in-home exercise being collected for analysis.

Referring now to FIG. 8A, an illustrative diagram of the cloud-based rehabilitation system and/or the "pressure" sensor rehabilitation system for use in leg rehabilitation. Herein, the in-home exercises may be directed to an ADL task being performed using one or more walking pads 800 with pressure sensors 810 within designated step areas. The walking pad(s) 800 is positioned around a support structure 820 (e.g., kitchen island, counter, kitchen table, etc.) to provide the patient with a structure for use to regain balance, if needed.

During the ADL and/or iADL task, performance data may be collected by the cameras $210_1$-$210_3$ positioned to capture patient movement surrounding the support structure 820. The movement data may be directed to metrics associated with gait, such as walking speed, smoothness, and lateral sway of the patient 215 during the ADL task. Concurrently, the pressure sensors 810 within the walking pad(s) 800 may be used to measure lateral sway and/or forward pitch based on pressure points applied to the sensors 810 by a patient's foot during the exercise. Additionally, the pressure sensors 810 within the walking pad(s) 800 may be used to determine a level of pronation or supination in foot placement, where a certain degree of overpronation or supination may suggest walking difficulties.

Figure 8B:
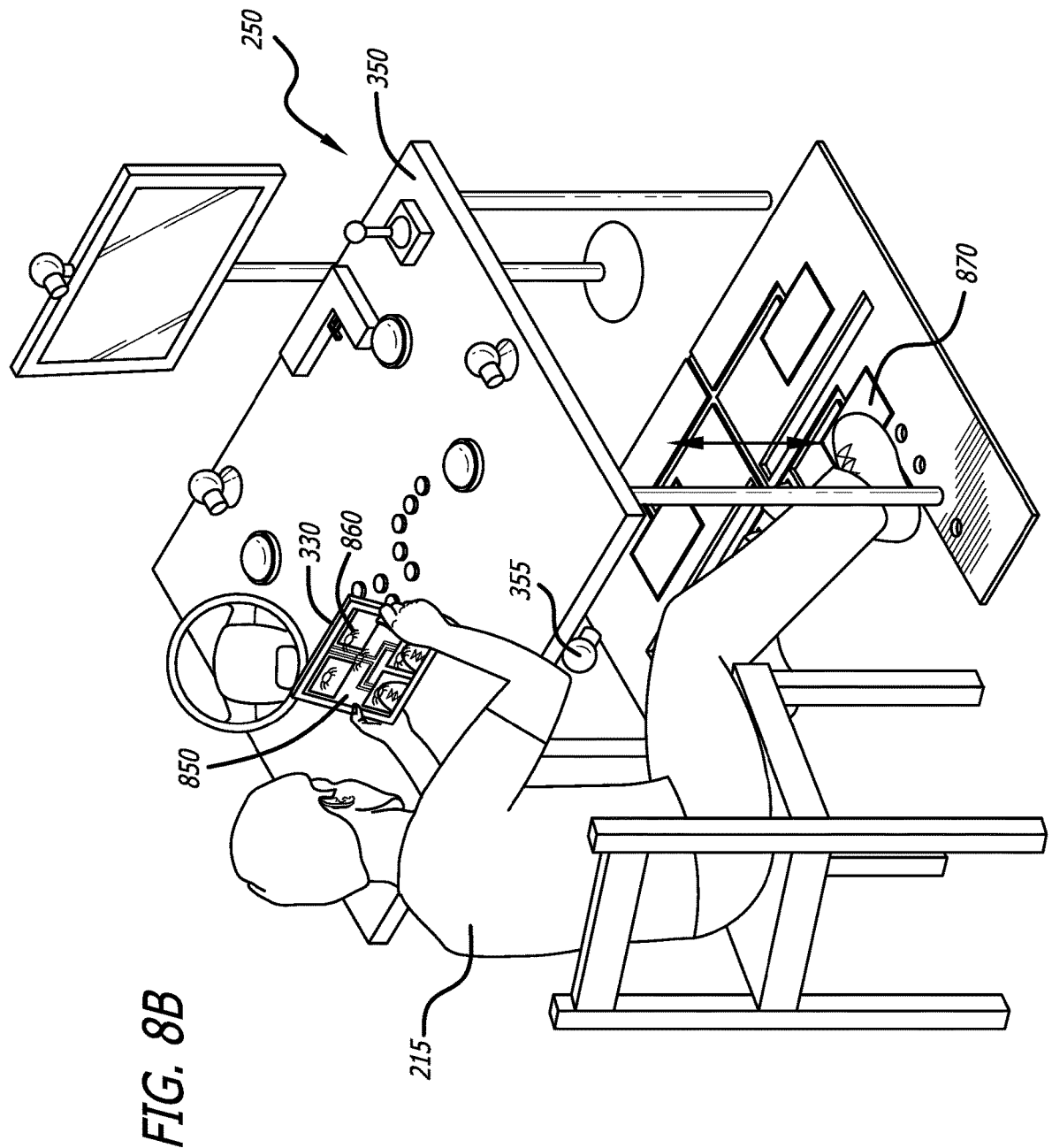
FIG. 8B is an illustrative diagram of a rehabilitation system including a patient workstation conducting an in-home exercise directed to leg rehabilitation and results of the in-home exercise being collected for analysis.

Referring now to FIG. 8B, an illustrative diagram of the patient workstation 250 for use in leg rehabilitation is shown. Herein, the in-home exercises may be directed to an ADL task being performed using the camera 355 positioned to capture an area 850 under the rehabilitation table 350 and display the area 850 on the second display 330. The second display 330 further receives computer-generated images 860 that overlay the area 850. More specifically, the computer-generated images 860 may include static images and/or moving images. Both of these virtual image types are visible upon viewing the second display 330. Therefore, the in-home exercise may display instructions or generate audible instructions to the patient 215 to perform recorded leg movement as the patient attempts to step on these computer-generated (virtual) images 860. The camera 355 may be further activated to capture the video associated with the patient's leg movement during the task and upload the video to the cloud service or network server that, knowing the placement of the virtual images 860, may assess the performance of the patient 215.

Additionally, it is contemplated that the virtual images 860 may be placed over pressure (touch) sensors 870. Hence, additional parameters may be measured such as the force applied to the "stomp" movement as well as flexibility of the foot in response to requests to stomp using your heel or toes, or the like.

Figure 9:
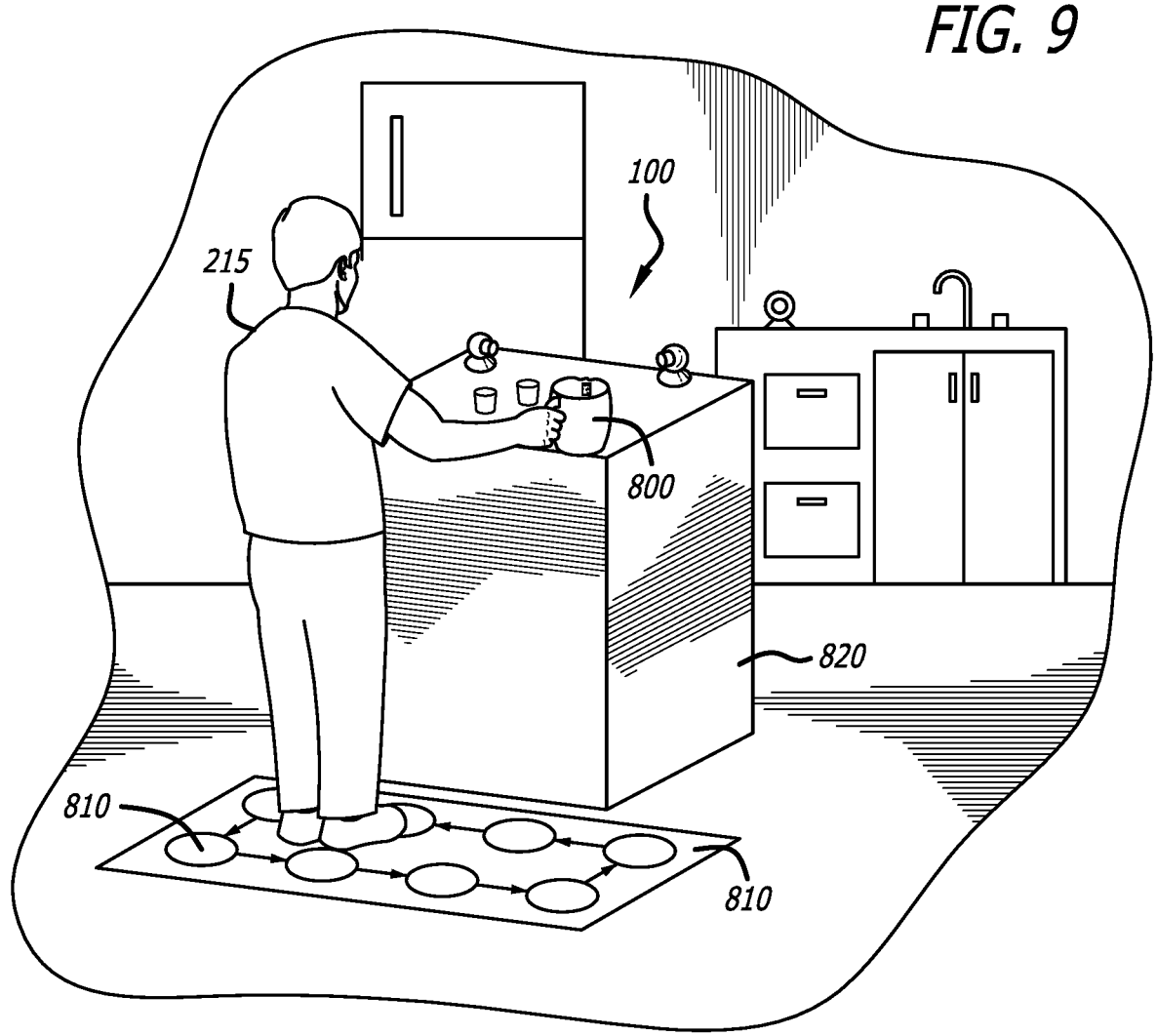
FIG. 9 is an illustrative diagram of a rehabilitation system conducting an in-home exercise directed to cognitive rehabilitation and results of the in-home exercise being collected for analysis.

As shown in FIG. 9, an exemplary diagram of the rehabilitation system 110 for use in cognitive rehabilitation is illustrated. Herein, the rehabilitation system features the walking pad(s) 800 with pressure sensors 810 within designated step areas. As before, the walking pad(s) 800 is positioned around the support structure 820 (e.g., kitchen island, counter, kitchen table, etc.). In addition to instructing the patient 215 to move along the walkway pattern stepping on the designated step patterns, the iADL task may be requesting the patient 215 to perform secondary tasks (e.g., slowly step at a particular location while pouting pour glass of water from a pitcher 900, walking along the walking pad(s) while singing a song, etc.). The multiple tasks are designed to improve cognitive ability.

Figures 10A, 10B:
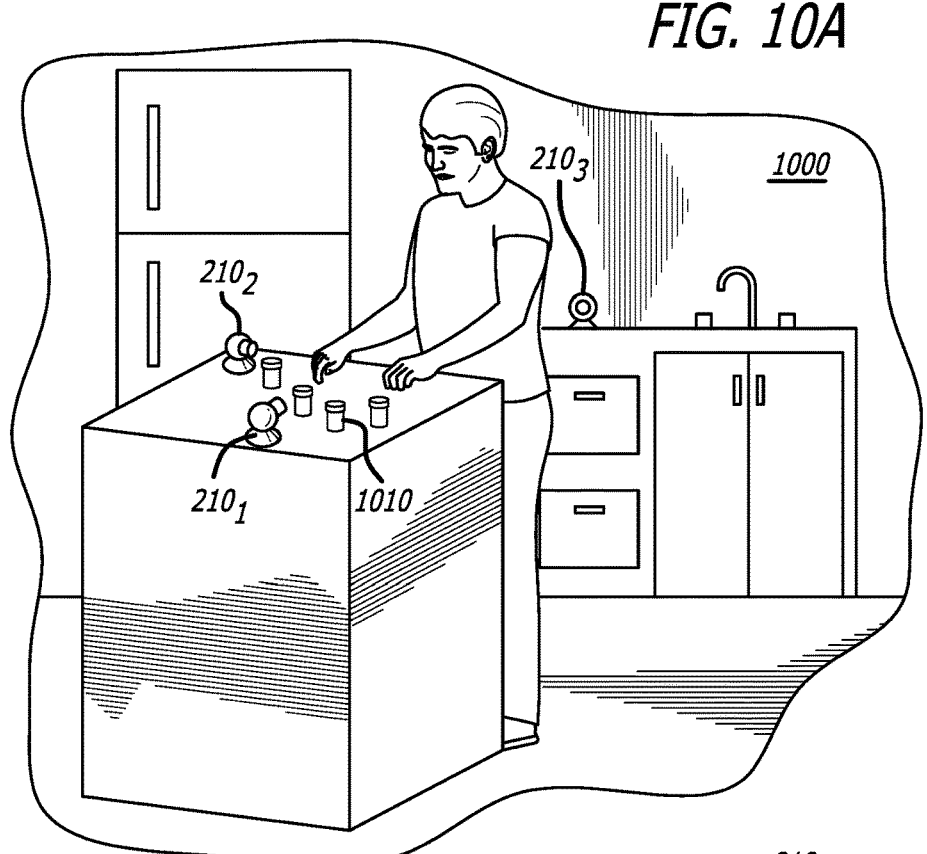
FIG. 10A is an illustrative diagram of a rehabilitation system conducting an in-home exercise directed to medicinal compliance verification.
FIG. 10B is an illustrative diagram of a rehabilitation system including a patient workstation conducting an in-home exercise directed to medicinal compliance verification.

Referring now to FIG. 10A, an illustrative diagram of the rehabilitation system of FIG. 2 for use in medicinal compliance verification is shown. Herein, the plurality of cameras $210_1$-$210_M$ are deployed within a room 1000. The cameras $210_1$-$210_M$ are configured to capture video directed to an iADL task such as medicinal compliance, where captured video from one or more of the cameras $210_1$-$210_M$ may be provided to cloud services or a computer accessible by a clinician to confirm medicinal compliance.

According to one embodiment of the disclosure, the patient 215 may receive instructions to perform an iADL task (e.g., take prescribed medicine) during his or her in-home exercises. These instructions may be provided as written or auditory instructions from the therapy software 235 hosted by the computing device 230 of a patient workstation 250 or from a remote network device (previously shown). During performance of the selected iADL task, one or more of the cameras $210_1$-$210_M$ may be activated to capture video continuously as the patient takes the prescribed medicine. The captured video may be analyzed to confirm medicinal compliance.

According to this embodiment of the disclosure, the patient 215 may receive instructions for take his or her medication. The instructions for taking the medication may be received from the clinician via a video conference call using the patient workstation 250, a video conference or audio communication via a device other than the patient workstation 250 such as a telephone, networked television, or the like. As the patient accesses a medicine bottle 1010 to obtain the requisite medicine available, one or more of the cameras $210_1$-$210_M$ may be under control of the clinician (via a remote connection such as Remote Desktop Access) or the clinician may simply obtain segments of video from the cameras $210_1$-$210_M$ that are continuously operating or operating based on controls initiated by the clinician or the patient.

Herein, the cameras $210_1$-$210_M$ are configured to monitor the actions and movements of the patient in order to provide video that is downloaded to the computing device 230 as shown in FIG. 2. In response to receive the video, the computing device may be adapted to perform any desired pre-processing operations (e.g., apply label to associate captured video with a particular task, insert markers into video to coordinate videos from different cameras and perspectives, etc.) to produce captured video content associated with medicinal intake. The captured video content is provided to the cloud service via a network. The automated analysis logic 134 of the cloud service 130 of FIG. 1, namely machine learning logic 262 or artificial neural network logic 264 for example, may be adapted to analyze the video such as compare segments of the captured video content against content associated with known activities when taking medicine (e.g., opening a medicine bottle, placing one or more pills into a hand, inserting one or more pills within a mouth, etc.). The known activities may be stored in a repository available to the automated analysis logic 134. Hence, the rehabilitation system 110 is equipped to confirm medicinal intake by the patient on a daily, weekly or monthly basis.

Referring to FIG. 10B is an illustrative diagram of the patient workstation 250 and sensor-based rehabilitation system operating in cooperation for medicinal compliance verification. Herein, as before, the plurality of cameras $210_1$-$210_M$ are deployed within a room. The cameras $210_1$-$210_M$ are configured to capture video directed to an iADL task such as medicinal compliance, where captured video from one or more of the cameras may be provided to cloud services or a computer accessible by a clinician to confirm medicinal compliance.

According to one embodiment of the disclosure, the patient 215 may receive instructions to perform an iADL task (e.g., take prescribed medicine) during his or her in-home exercises. Again, these instructions may be provided as written or auditory instructions via the computing device 230 of the patient workstation 250 or from a remote network device (not shown). During performance of the selected iADL task, by removal of a cap 1050 of a smart cap medicine bottle 1060, a wireless signal 1070 (e.g., Bluetooth signal) may be transmitted directly or indirectly (via computing device 230) to activate one or more of the cameras $210_3$-$210_6$ as the patient takes the prescribed medicine. The captured video content may be analyzed to confirm medicinal compliance.

According to another embodiment of the disclosure, however, the patient 215 may receive instructions for take his or her medication directly from a clinician (e.g., via video conference call using the patient workstation 250, video conferencing or audio communication via a device other than the patient workstation 250 such as a telephone, networked television, or the like). As the patient accesses the smart capped medicine bottle 1050 to obtain the requisite medicine available, where signaling is provided from the cap 1060 to one or more of the cameras $210_3$-$210_6$ upon separation of the cap 1060 from the medicine bottle 1050. The clinician may simply obtain segments of video from the one or more cameras $210_3$-$210_6$ (e.g., camera $210_6$) provided to the computing device 230 or video segments received based on controls initiated by the clinician or the patient.

Herein, the cameras $210_3$-$210_6$ are configured to monitor the actions and movements of the patient in order to provide the captured video content to the computing device 230. In response to receive the video, the computing device 230 may be adapted to perform any desired pre-processing operations (e.g., apply label to associate captured video with a particular task, insert markers into video to coordinate videos from different cameras and perspectives, etc.) to produce the captured video content associated with medicinal intake. The captured video content is downloaded from the computing device 230 to the cloud service 130 via a network. The automated analysis logic 134 of the cloud service 130, namely machine learning logic 262, artificial neural network (ANN) logic 262, and other artificial intelligence logic, that is adapted to analyze the video such as compare segments of the video content against content associated with known activities when taking medicine (e.g., opening a medicine bottle, placing one or more pills into a hand, inserting one or more bills within a month, etc.). Each video segment of the video may be a series of frames, a single frame, or a portion of a frame. The known activities and/or abnormal activities may be stored in a repository available to the automated analysis logic 134. Such data may allow ML or CNN to confirm medicinal intake by the patient on a daily, weekly or monthly basis.

The system described in the foregoing provides many advantages not provided by current rehabilitation therapy solutions. For one thing, the system provides a holistic approach to rehabilitation therapy that focuses on in-home exercises directed to ADL and/or iADL tasks: recovery of function and independence is related to patient knowledge, patient empowerment, and prevention of known potential complications. Moreover, the system can be used for patients having a variety of conditions as well as degrees of impairment.

The system is modular and open to reconfiguration and personalization. The same system can be used to treat patients with many different diagnoses and can be adjusted and personalized (by the clinician, patient, or both) to be useful to persons with any degree of disease severity. This also means that, as a patient improves, treatment through this system can be adjusted to remain useful.

The system can be used to provide rehabilitation therapy in many different settings that can be remote from the clinician. Because the system is portable and transportable, the same rehabilitation therapy can be provided in the home, clinic, or any other setting.

The treatment provided by the system can be remotely reviewed and/or revised by persons providing rehabilitation care. The communication components of this system enable a remote clinician to input progress reports and other forms of patient data and to output a revised treatment plan that is uploaded silently and rapidly to the patient's workstation.

The system also opens the door to providing the same rehabilitation therapy to a given patient across different locations, e.g., from rehabilitation hospital to skilled nursing facility to one home to another home, anywhere in the world. Smoothing transitions in rehabilitation care is a major plus provided by the system, as problems during transitions of care account for a disproportionate extent of adverse events and readmissions, which are topics that attain great significance in the Affordable Care Act and Accountable Care Organizations era. Improvements in the continuity of care for patients moving through the stages of rehabilitation therapy can also improve short-term and long-term therapist-patient relations. This system is specifically designed to promote favorable forms of recovery by employing known principles of neural plasticity and motor learning including high intensity therapy that allows for hundreds of movement repetitions, keeping the patient continuously challenged at an individualized level, variability, high interest and motivation, and regular provision of feedback.

The system further provides the experience needed to maximize effects from neuromodulatory treatments. For many treatments that aim to modulate neural function after a brain injury, such as medications or brain stimulation, abundant data suggests that treatment effects require concomitant behavioral training or shaping. Recovery treatments require experience-dependent brain plasticity and the disclosed system is well suited to apportion, provide, and measure the rehabilitation experience.

The system also provides improved motivation to patients for them to practice their assigned rehabilitation activities. Motivation of patients is improved by the system in at least in seven ways: (1) tailoring the in-home exercises to actual ADL and/or iADL tasks to accelerate achievement of independent living or identify where assistance is needed; (2) flexible and continuous tailoring of in-home exercises to provide excessive challenges and boredom; (3) multiple data types for use in evaluation and automated analysis to provide reduced workload on the clinician to allow him or her to service more patients and/or focus more attention on rehabilitation regimen; (4) confirm proper medicinal application; (5) record performance of the ADL and/or iADL tasks and medicinal compliance that may be useful to the patient, clinician, and third-party payers; (6) reliance on fun games to drive compliance; and (7) implementation of individualized behavior change techniques and health regulatory focus.

The system further provides a broad standardization of care. Some forms of rehabilitation therapy benefit from provision in a standardized manner. Whether using a single central care provider or multiple providers, the system facilitates this, for example, providing the same form of therapy to many patients who are scattered over time and space.

The system also provides a quantitative measurement of quality of patient performance. Patients and clinicians are provided with several measures of patient performance, progress, and improvements/declines. This provides information regarding a patient's impairments and functional status, and reveals how these change over time. The use of multiple assessment instruments, methods, and devices provides a broad view of patient status and a more comprehensive profile than any single measurement approach.

The system further provides quantitative measurement of amount of patient performance in terms of information regarding how much therapy a patient is actually performing with the system. Such data can be valuable to a clinical trial where measurement of number of minutes of therapy each day is a critical variable or to an insurance carrier that wishes to confirm patient compliance justifies a rehabilitation expense.

The system also provides patient accountability. In some settings, rehabilitation therapy is a valuable commodity. Therefore, in such settings, rehabilitation therapy might be most judiciously provided in relation to effective utilization. Having a patient be accountable can allow the provider of care, such as an insurance carrier, to measure how the patient is contributing to his/her own care, and apportion therapy based on this measure of accountability.

The system can further provide feedback that can come in many forms, be in real time, and be used to improve future performances. As an extension of this, real-time measures of patient performance can be used to adjust the difficulty level of rehabilitation games and exercises on the fly according to pre-selected rules. The system enables the user to interface with many current rehabilitation devices. As noted above, the system includes many games, which can be used with a range of different rehabilitation devices. Numerous devices can be adapted in this regard, including most or all commercially available rehabilitation devices.

The system also can generate regular progress reports, which can focus on patient goals, therapist goals, or feedback (to patient or therapist) of patient performance and usage statistics. Such reports can be in real time or retrospective, and can cover data over a minute, an hour, a day, or a year's efforts. In this way, the system introduces a means to generate objective, quantitative documentation of a patient's home rehabilitation efforts.

The system also enables internet-based communication. The communication components of the system allow live videoconference dialogues between patients and clinicians. In addition, the communication components enable remote assessments for clinical trials. An issue that plagues many clinical trials is obtaining outcome measures in a consistent manner. Variance in outcomes measurements can overshadow treatment effects. The disclosed system provides a solution to this issue by having only one, or by having only a small number, of raters perform assessments, centrally. This also allows only persons with high expertise to perform the assessments, thereby reducing variance due to many people of many skill levels doing outcomes assessments.

Some forms of rehabilitation therapy are best, or can only be, accomplished in a group setting, such as certain games that involve multiple players or patients, whether taking turns on a shared workstation, or when playing games on workstations connected by a network. Also, group interactions have social value that impact psychological aspects of disability, including psychological aspects of motor dysfunction after stroke. Art therapy, chatrooms, and support groups are all potential examples of how the disclosed system may be used for multi-patient interactions. This type of interaction addresses key psychosocial issues important to patient recovery.

The system further can be used for vocational training. When desired, features of the system can be tailored to emphasize activities that are related to job training and re-entering of the marketplace.

A number of principles of rehabilitation and plasticity have been incorporated into the content of rehabilitation system, such as incorporation of motor imagery, motor observation, inclusion of bilateral movements, sensory stimulation prior to movement practice, incorporation of music, incorporation of meditation and confidence building, mirror therapy, modulation of attention to task, contextual interference, cueing, socialization, enriched environment, provision of feedback, and gameifying to increase enjoyment, motivation, and compliance.

The system can further be used to educate patients. The system maximizes patient engagement in their own care by providing information about their underlying disease. This helps improve overall health, for example, by prevention of secondary complications and by improving risk factor management. The system can also be used to educate therapists. For example, the system can be used to deliver education such as webinars to clinicians who use the system, for example, by experts from around the world. Education can further extend to caregivers. A patient's caregiver, such as their spouse, plays an important role in rehabilitation and recovery. This system can help educate or provide support for a caregiver.

What is claimed is:

1. A portable patient workstation configured to facilitate in-home rehabilitation therapy, the workstation comprising:
    a computing device configured to generate computer-based tasks associated with one or more in-home exercises;
    a tabletop console communicatively coupled to the computing device, the tabletop console comprising a mat and one or more user interface devices mounted to the mat, wherein the one or more user interface devices are communicatively coupled to the computing device, wherein the one or more user interface devices include a first plurality of buttons positioned on the mat and spaced apart so as to define four corners of a rectangular space on a surface of the mat, and a second plurality of buttons adjacent to each other and arranged in two lateral rows positioned within the rectangular space, wherein the lateral rows are biased towards one edge of the rectangular space, wherein the lateral rows are curved so as to ergonomically receive the patient's fingertips, wherein the first plurality of buttons are larger in size than the second plurality of buttons, wherein the first plurality of buttons are adapted to illuminate; and
    one or more rehabilitation devices communicatively coupled to the computing device, the one or more rehabilitation devices include a first rehabilitation device including a sensor that captures performance data for use in evaluating a patient's motor skills when instructed to perform one or more of the tasks,
    wherein the performance data includes metric information associated with a subset of a plurality of prescribed metrics, the plurality of prescribed metrics include at least two of (i) a measured direction of movement, (ii) a measured distance of movement, (iii) a measured amount of rotation, (iv) a measure of velocity at least one of linear and angular velocity, and (v) a measure of acceleration including at least one of linear and angular acceleration of the sensor.

2. The patient workstation of claim 1, wherein the sensor being integrated within the first rehabilitation device.

3. The patient workstation of claim 1, wherein the sensor being adapted for insertion into a cavity sized for housing and retention of the sensor within the first rehabilitation device.

4. The patient workstation of claim 1 further comprising:
    one or more displays electrically connected to the computing device;
    a network interface device communicatively coupled to the computing device, the network interface device to transmit information from and receive information directed to the patient workstation via a network.

5. The patent workstation of claim 4 being communicatively coupled to a plurality of cameras positioned proximal to the computing device.

6. The patient workstation of claim 5, wherein the network interface device is communicatively coupled to a cloud service that analyzes video content captured by the plurality of cameras.

7. The patient workstation of claim 1 further comprising one or more displays electrically connected to the computing device, a first display of the one or more displays supports an augmented reality operation that operates in combination with the first rehabilitation device in providing a task of the one or more tasks to be performed on an object created during the augmented reality operation.

8. The patient workstation of claim 1, wherein at least a first rehabilitation device of the one or more rehabilitation devices comprises the sensor including a communication transceiver, an accelerometer, and a gyroscope and compass component set.

9. The patient workstation of claim 8, wherein the accelerator and gyroscope and compass component set are adapted to measure changes in movement of the first rehabilitation device.

10. The patient workstation of claim 8, wherein the sensor is removably coupled to the first rehabilitation device.

11. The patient workstation of claim 1, wherein the computing device is configured to receive the captured performance data and transmit the performance data to a private cloud service including machine learning logic or artificial neural network logic that automatically, without human intervention, analyzes the performance data to evaluate the patient's motor skills.

12. A portable patient workstation comprising:
    a computing device;
    a table-top console communicatively coupled to the computing device, the tabletop console comprising a mat and one or more user interface devices mounted to the mat, wherein the one or more user interface devices are communicatively coupled to the computing device and adapted to receive patient inputs, wherein the one or more user interface devices include a first plurality of buttons positioned on the mat and spaced apart so as to define four corners of a rectangular space on a surface of the mat, and a second plurality of buttons adjacent to each other and arranged in two lateral rows positioned within the rectangular space, wherein the lateral rows are biased towards one edge of the rectangular space, wherein the lateral rows are curved so as to ergonomically receive the patient's fingertips, wherein the first plurality of buttons are larger in size than the second plurality of buttons, wherein the first plurality of buttons are adapted to illuminate;

one or more rehabilitation devices including a first rehabilitation device that comprises a sensor that captures performance data; and wherein the computing device is configured to receive performance data from the one or more rehabilitation devices and patient input data from the table-top console, the performance data and the patient input data being for use in evaluating a patient's motor skills when instructed to perform one or more of the tasks, wherein the portable patient workstation is used for neuromodulatory treatment of the patient, wherein the portable patient workstation treatment allows for adjustment of said treatment as the patient improves.

13. The patient workstation of claim 12, wherein the sensor being integrated within the first rehabilitation device.

14. The patient workstation of claim 12, wherein the sensor being adapted for insertion into a cavity sized for housing and retention of the sensor within the first rehabilitation device.

15. The patient workstation of claim 12 further comprising:

a first display electrically connected to the computing device to display augmented reality images for use in evaluating the patient's motor skills.

16. The patent workstation of claim 12 further comprising a plurality of cameras positioned proximal to the computing device to capture video for use by machine learning logic in evaluating the patient's motor skills.

17. The patient workstation of claim 12, wherein the first rehabilitation device comprises the sensor including a communication transceiver, an accelerometer, and a gyroscope and compass component set.

18. The patient workstation of claim 17, wherein the accelerator and the gyroscope and compass component set are adapted to measure changes in movement of the first rehabilitation device.

19. The patient workstation of claim 17, wherein the sensor is removably coupled to the first rehabilitation device.

* * * * *